United States Patent
Kobayashi et al.

(10) Patent No.: US 11,006,634 B2
(45) Date of Patent: May 18, 2021

(54) ANTIBACTERIAL GLASS

(71) Applicant: KOA GLASS CO., LTD, Tokyo (JP)

(72) Inventors: Yoshinao Kobayashi, Tokyo (JP); Kunihiko Nemoto, Tokyo (JP)

(73) Assignee: KOA Glass Co., Ltd., Tokyo (JP)

( * ) Notice: Subject to any disclaimer, the term of this patent is extended or adjusted under 35 U.S.C. 154(b) by 0 days.

(21) Appl. No.: 15/986,152

(22) Filed: May 22, 2018

(65) Prior Publication Data
US 2018/0263244 A1    Sep. 20, 2018

Related U.S. Application Data

(63) Continuation of application No. 14/889,729, filed as application No. PCT/JP2014/063940 on May 27, 2014, now abandoned.

(51) Int. Cl.
| | | |
|---|---|---|
| *A01N 59/16* | (2006.01) | |
| *A01N 25/34* | (2006.01) | |
| *A01N 59/26* | (2006.01) | |
| *C03C 3/17* | (2006.01) | |
| *C03C 3/19* | (2006.01) | |
| *C02F 1/50* | (2006.01) | |
| *A61L 2/16* | (2006.01) | |
| *C02F 1/68* | (2006.01) | |
| *A01N 59/06* | (2006.01) | |
| *D06F 35/00* | (2006.01) | |
| *C03C 4/00* | (2006.01) | |
| *D06F 39/00* | (2020.01) | |
| *D06F 39/02* | (2006.01) | |
| *C02F 101/30* | (2006.01) | |
| *C02F 103/00* | (2006.01) | |

(52) U.S. Cl.
CPC ............ *A01N 59/16* (2013.01); *A01N 25/34* (2013.01); *A01N 59/06* (2013.01); *A01N 59/26* (2013.01); *A61L 2/16* (2013.01); *C02F 1/50* (2013.01); *C02F 1/505* (2013.01); *C02F 1/688* (2013.01); *C03C 3/17* (2013.01); *C03C 3/19* (2013.01); *C03C 4/0007* (2013.01); *D06F 35/008* (2013.01); *D06F 39/00* (2013.01); *C02F 2101/30* (2013.01); *C02F 2103/002* (2013.01); *C02F 2303/04* (2013.01); *C02F 2307/12* (2013.01); *C03C 2204/02* (2013.01); *D06F 39/024* (2013.01); *Y02W 10/37* (2015.05)

(58) Field of Classification Search
CPC ...................................................... A01N 59/16
See application file for complete search history.

(56) References Cited

U.S. PATENT DOCUMENTS

| | | |
|---|---|---|
| 6,528,443 B1 | 3/2003 | Healy |
| 6,555,491 B1 | 4/2003 | Healy |
| 8,080,490 B2 | 12/2011 | Fechner |
| 2001/0023156 A1 | 9/2001 | Nomura |
| 2005/0233888 A1 | 10/2005 | Scott |
| 2010/0004111 A1 | 1/2010 | Kobayashi et al. |
| 2012/0015018 A1 | 1/2012 | Kobayashi |

FOREIGN PATENT DOCUMENTS

| | | | |
|---|---|---|---|
| CN | 1771207 A | * | 5/2006 |
| EP | 1116698 | | 7/2001 |
| EP | 1116700 | | 7/2001 |
| EP | 1452496 | | 9/2004 |
| EP | 2430922 | | 3/2012 |
| JP | 1994100329 A | | 4/1994 |
| JP | 07063701 A | | 7/1995 |
| JP | 1995300339 A | | 11/1995 |
| JP | 2001247333 A | | 9/2001 |
| JP | 2002037643 A | | 2/2002 |
| JP | 2002516811 A | | 6/2002 |
| JP | 2002516812 A | | 6/2002 |
| JP | 2005255517 A | | 9/2005 |
| JP | 2008231005 A | | 10/2008 |
| JP | 2012007870 A | | 1/2012 |
| WO | WO2005087575 | | 9/2005 |

OTHER PUBLICATIONS

Extended European Search Report dated Oct. 14, 2016 for European Patent Application No. 14819318.8.

* cited by examiner

*Primary Examiner* — Sarah Alawadi
(74) *Attorney, Agent, or Firm* — Renner, Kenner; Arthur M. Reginelli

(57) ABSTRACT

An antimicrobial glass tablet that releases silver ions when brought into direct contact with water, containing: $Ag_2O$ within the range of above 5% by weight but less than 10% by weight, ZnO below 10% by weight, $P_2O_5$, CaO, $K_2O$, $Al_2O_3$, and MgO.

8 Claims, 17 Drawing Sheets

ANTIBACTERIAL GLASS

This application is a continuation application of U.S. application Ser. No. 14/889,729 filed on Nov. 6, 2015, which is a National-Stage Application of PCT Application No. PCT/JP2014/063940 filed on May 27, 2014, and claims the benefit of JP Application No. JP2013-138575 filed on Jul. 2, 2013, which are incorporated herein by reference.

TECHNICAL FIELD

The present invention relates to an antimicrobial glass, in particular, an antimicrobial glass which can be accommodated in a narrow accommodation space of an antimicrobial water unit for supplying antimicrobial water to a washing tub of a washing machine, and can effectively suppress an occurrence of black mold or the like in a washing tub and can effectively protect a subject for washing against microbes while suppressing the coloration.

BACKGROUND ART

Conventionally, for preventing propagation of bacteria or mold in water stored in a water storage tank or a drain pan of an air conditioner or the like, an antimicrobial glass exhibiting an antimicrobial effect by releasing silver ions into water when brought into direct contact with water has been broadly used.

Furthermore, for the antimicrobial glass used for such application, a predetermined elution amount of silver ions needs to be maintained over a long period of time, and thus various modifications, for example, the composition or size of the antimicrobial glass is modified to a predetermined range or a pH fluctuation of water is suppressed by using in combination plural antimicrobial glasses with different properties, have been made to satisfy such needs (for example, see Patent Document 1 and Patent Document 2).

Specifically, disclosed in Patent Document 1 is, as a soluble glass containing at least one element selected from metallic ions of $Ag^+$, $Cu^+$, $Cu^{2+}$, and $Zn^{2+}$, a glass water treatment material characterized in that it has right hexahedral, cubic, flat, or spherical three-dimensional shape and its largest diameter is 10 mm or more and its composition has weight ratios of $(RO+R_2O)/P_2O_5=0.4$ to 1.2 and $R_2O/(RO+R_2O_3)=0$ to 10, the dissolution speed (A) at an initial stage (a period corresponding to initial 20% of the time period from start of dissolution to dissolution of the entire amount, the same shall apply hereinafter) and the dissolution speed (B) at a final stage (on contrary to the initial period, it indicates a period corresponding to final 20%, the same shall apply hereinafter) have a relationship of $B/A \geq \frac{1}{3}$, and the content of the metallic ions is 0.005 to 5% by weight.

Furthermore, disclosed in Patent Document 2 is a mixed antimicrobial glass for an air conditioning system, exhibiting an antimicrobial effect by releasing silver ions therefrom in the air conditioning, including an antimicrobial glass exhibiting an alkaline property when dissolved and an antimicrobial glass exhibiting an acid property when dissolved, an elution amount of silver ions, which is measured under a prescribed measurement condition, of the antimicrobial glass exhibiting an alkaline property, and an elution amount of silver ions, which is measured under a prescribed measurement condition, of the antimicrobial glass exhibiting an acid property are respectively values within the range of 0.005 to 1 mg/(g·1 liter·24 Hrs·30° C.), a blending amount of the antimicrobial glass exhibiting an alkaline property to 100 parts by weight of the antimicrobial glass exhibiting an acid property is a value within the range of 10 to 120 parts by weight, and the total elution amount of silver ions measured under the prescribed measurement condition is a value within the range of 0.01 to 5 mg/(g·1 liter·24 Hrs·30° C.)

In Patent Document 2, there is also a description suggesting that the antimicrobial glass exhibiting an acid property when dissolved preferably has the composition in which it contains $Ag_2O$, $MgO$, $K_2O$, $ZnO$ and $P_2O_5$ as a raw material, and when the total amount is 100% by weight, the content of $Ag_2O$ has a value within the range of above 5% by weight but less than 10% by weight, the content of $MgO$ has a value within the range of 3 to 10% by weight, the content of $K_2O$ has a value within the range of 5 to 20% by weight, the content of $ZnO$ has a value within the range of 10 to 25% by weight, and the content of $P_2O_5$ has a value within the range of 55 to 75% by weight, and when the total amount is less than 100% by weight, other glass components (for example, alkali metal oxide, alkali earth metal oxide, $CeO_2$, $Al_2O_3$, $CoO$, or the like) are contained, as a residual component, within the range of 0.1 to 37% by weight.

CITATION LIST

Patent Document

Patent Document 1: JP 7-63701 A (Claims and the like)
Patent Document 2: JP 2012-7870 A (Claims and the like)

DISCLOSURE OF THE INVENTION

Problem to be Solved by the Invention

However, according to the glass water treatment material described in Patent Document 1, the content of metal ions which exhibit an antimicrobial effect is limited to 0.005 to 5% by weight. As such, there is a problem that, in order to increase the elution amount of metal ions, a large amount of the glass water treatment material has to be added to water.

In particular, for supplying antimicrobial water to a washing tub of a washing machine, it is required to protect a subject for washing against microbes but also to prevent an occurrence of black mold or the like in the washing tub.

Thus, it is required to elute, within a short period of time, at least predetermined amount of metal ions to a large amount of water, and to satisfy such requirement, it is necessary to use a large amount of a glass water treatment material.

Meanwhile, for having a small size and an improved design of a washing machine as a whole, an antimicrobial water unit for supplying antimicrobial water to a washing tub of a washing machine is configured to be very small. As such, there is a problem that it is not possible to have a space enough for accommodating a large amount of a glass water treatment material.

As such, the glass water treatment material described in Patent Document 1 has a problem that it is difficult to be used for an application for supplying antimicrobial water to a washing tub of a washing machine.

Furthermore, in the antimicrobial glass exhibiting an acidic property when dissolved as described in Patent Document 2, the content of $Ag_2O$ as a basis of silver ion is more than 5% by weight but less than 10% by weight, and thus the elution amount of silver ions can be increased without adding a large amount of an antimicrobial glass to water, and also it is possible to apply the antimicrobial glass for supplying antimicrobial water to a washing tub of a washing machine.

However, because the antimicrobial glass exhibiting an acidic property when dissolved as described in Patent Document 2 is supposed to be used in combination with an antimicrobial glass exhibiting an alkaline property when dissolved, if it is used singly, the dissolution speed becomes excessively high, and thus there is a problem that it is difficult to maintain a predetermined elution amount of silver ions over a long period of time.

Furthermore, as the dissolution speed becomes excessively high, the elution amount of silver ions also excessively increases so that there is also a problem that coloration of a subject for washing is easily caused by excessive silver ions.

Accordingly, the inventors of the present invention conducted intensive studies in view of the aforementioned problems. As a result, it was found that, when the composition of an antimicrobial glass which releases silver ions when brought into direct contact with water is set to a predetermined composition and the shape and maximum diameter of the glass are adjusted to be in a predetermined range, it is possible to obtain an antimicrobial glass which can stably maintain a predetermined elution amount of silver ions over a long period of time, even if it is a compact amount. The present invention is completed accordingly.

Namely, an object of the present invention is, in particular, an antimicrobial glass which can be accommodated in a narrow accommodation space in an antimicrobial water unit for supplying antimicrobial water to a washing tub of a washing machine, can effectively suppress an occurrence of black mold or the like in a washing tub, and can effectively protect a subject for washing against microbes while suppressing coloration of the subject.

Means for Solving Problem

According to the antimicrobial glass of the present invention, an antimicrobial glass for exhibiting an antimicrobial effect by releasing silver ions when brought into direct contact with water, in which it contains $Ag_2O$, $P_2O_5$, CaO, ZnO, $K_2O$, $Al_2O_3$, and MgO as a raw material, and when the total amount is 100% by weight, the content of $Ag_2O$ has a value within the range of above 5% by weight but less than 10% by weight, the content of $P_2O_5$ has a value within the range of 55 to 75% by weight, the content of CaO has a value within the range of 1 to 10% by weight, the content of ZnO has a value of below 10% by weight, the content of $K_2O$ has a value within the range of 5 to 20% by weight, the content of $Al_2O_3$ has a value within the range of 1 to 10% by weight, and the content of MgO has a value within the range of 5 to 20% by weight, and the antimicrobial glass has a tablet shape with a maximum diameter value within the range of 5 to 20 mm, is provided to solve the aforementioned problems.

Namely, according to the antimicrobial glass of the present invention, the composition of the glass is set to a predetermined composition and the shape and maximum diameter of the glass are adjusted to be in a predetermined range, and thus it is possible to stably maintain a predetermined elution amount of silver ions over a long period of time, for example, ten years or longer, even if it is a compact amount.

Thus, according to the antimicrobial glass of the present invention, in particular, it is possible to have accommodation in a narrow accommodation space in an antimicrobial water unit for supplying antimicrobial water to a washing tub of a washing machine, effective suppression of an occurrence of black mold or the like in a washing tub, and effective protection of a subject for washing while suppressing coloration of the subject.

Furthermore, for configuring the antimicrobial glass of the present invention, it is preferable that the specific surface area of the antimicrobial glass has a value within the range of 0.1 to 5 cm$^2$/g.

By having this configuration, the predetermined amount of silver ions can be more stably maintained over a long period of time.

For configuring the antimicrobial glass of the present invention, the silver ion elution amount measured for the antimicrobial glass by the following measurement conditions (hereinbelow, referred to as reference silver ion elution amount) is preferably a value within the range of 0.025 to 0.1 mg/(g·1 liter·24 Hrs·30° C.)

Measurement Conditions 30 g of the antimicrobial glass as a subject for measurement is immersed in 1 liter of purified water (30° C., pH 6.5) and kept in a closed system for 24 hours with the temperature maintained followed by measurement.

By having this configuration, a predetermined silver ion elution amount can be more stably maintained over a long period of time.

Furthermore, for configuring the antimicrobial glass of the present invention, when the contents of the ZnO and $Al_2O_3$ are C1 (% by weight) and C2 (% by weight), respectively, the C2/C1 is preferably a value of 0.4 or more.

By having this configuration, a predetermined silver ion elution amount can be more stably maintained over a long period of time.

Furthermore, for configuring the antimicrobial glass of the present invention, accommodation is preferably made inside a coated member which is provided with an opening for passing water therethrough, By having this configuration, not only the handling is improved but also the release caused by flowing water can be prevented even when the antimicrobial glass is reduced to a small size due to use for a long period of time.

Furthermore, for configuring the antimicrobial glass of the present invention, accommodation is preferably made, together with a non-antimicrobial glass, inside a coated member.

By having this configuration, adhesion between antimicrobial glasses are prevented so that a predetermined silver ion elution amount can be more stably maintained over a long period of time.

Furthermore, for configuring the antimicrobial glass of the present invention, it is preferably an antimicrobial glass for a washing machine to be accommodated in an antimicrobial water unit for supplying antimicrobial water to a washing tub of a washing machine.

By having this configuration, not only the accommodation can be made in a narrow accommodation space in an antimicrobial water unit for supplying antimicrobial water to a washing tub of a washing machine but also effective suppression of an occurrence of black mold or the like in a washing tub and effective protection of a subject for washing against microbes can be achieved while suppressing coloration of the subject.

BEST MODE(S) FOR CARRYING OUT THE INVENTION

The embodiment of the present invention relates to an antimicrobial glass for exhibiting an antimicrobial effect by releasing silver ions when brought into direct contact with water, characterized in that it contains $Ag_2O$, $P_2O_5$, CaO, ZnO, $K_2O$, $Al_2O_3$, and MgO as a raw material, and when the total amount is 100% by weight, the content of $Ag_2O$ has a value within the range of above 5% by weight but 10% by weight or less, the content of $P_2O_5$ has a value within the range of 55 to 75% by weight, the content of CaO has a value within the range of 1 to 10% by weight, the content of ZnO has a value of below 10% by weight, the content of $K_2O$ has a value within the range of 5 to 20% by weight, the content of $Al_2O_3$ has a value within the range of 1 to 10% by weight, and the content of MgO has a value within the range of 5 to 20% by weight, and the antimicrobial glass has a tablet shape with a maximum diameter value within the range of 5 to 20 mm.

Hereinbelow, the antimicrobial glass as an embodiment of the present invention is specifically described with appropriate reference to the drawings.

Meanwhile, hereinbelow, the antimicrobial glass of the present invention is described basically as an antimicrobial glass for a washing machine. However, the antimicrobial glass of the present invention is not limited to an antimicrobial glass for a washing machine, and it is also applicable to, for example, a water storage tank of equipment or products for keeping water for a predetermined period, such as a water purifier, a humidifier, an air cleaner, and a nozzle cleaner of a warm-water cleaning toilet seat.

1. Application to Washing Machine

The antimicrobial glass of the present invention is preferably an antimicrobial glass for a washing machine which is installed in an antimicrobial water unit for supplying antimicrobial water to a washing tub of a washing machine.

This is because, as described specifically hereinbelow, the antimicrobial glass of the present invention has a predetermined composition and the shape and maximum diameter that are within a predetermined range, and thus it can stably maintain a predetermined silver ion elution amount over a long period of time, even if it is a compact amount.

As such, regarding the antimicrobial glass of the present invention, it can be stored in a narrow accommodation space in an antimicrobial water unit for supplying antimicrobial water to a washing tub of a washing machine, can effectively suppress an occurrence of black mold or the like in a washing tub, and can effectively protect a subject for washing against microbes while suppressing coloration of the subject.

Figure 1A:
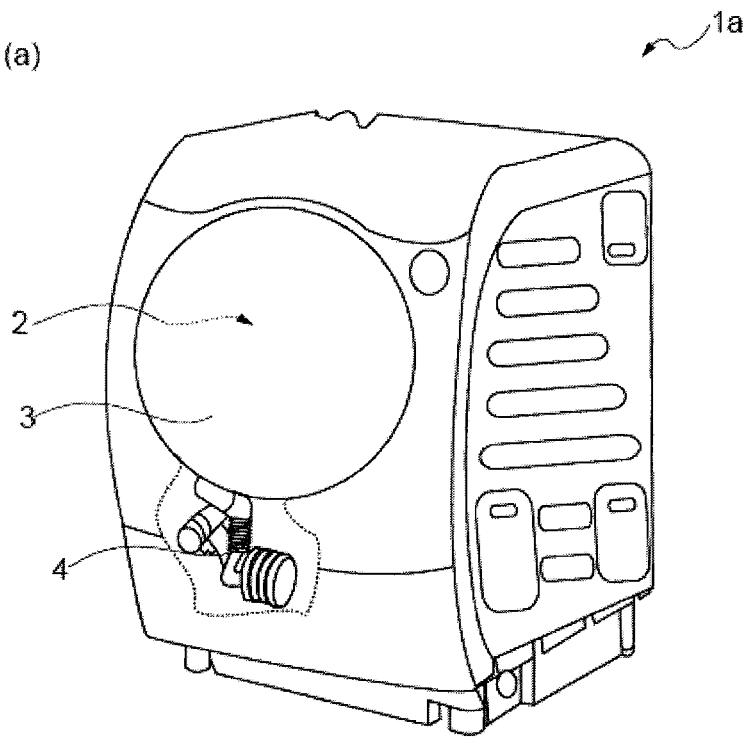
FIG. 1(a) and FIG. 1(b) are drawings which are provided for describing a location for installing an antimicrobial water unit in a washing machine.

Namely, the antimicrobial water unit in a drum type washing machine 1a is installed, for example, on an inner wall side of a circulating water path 4 for draining washing water inside a washing tub 2, which is installed inside a cover 3, to outside, purifying the washing water by collecting threads or the like in the washing water, and circulating it back to the washing tub 2, as shown in FIG. 1(a).

The circulating water path 4 is installed, from the viewpoint of saving water, to recycle the washing water as much as possible.

As the antimicrobial water unit is installed on the inner wall side of the circulating water path 4, silver ions can be constantly released to washing water circulating the circulating water path 4 so that it becomes possible to supply efficiently the antimicrobial water to the washing tub 2.

Figure 1B:
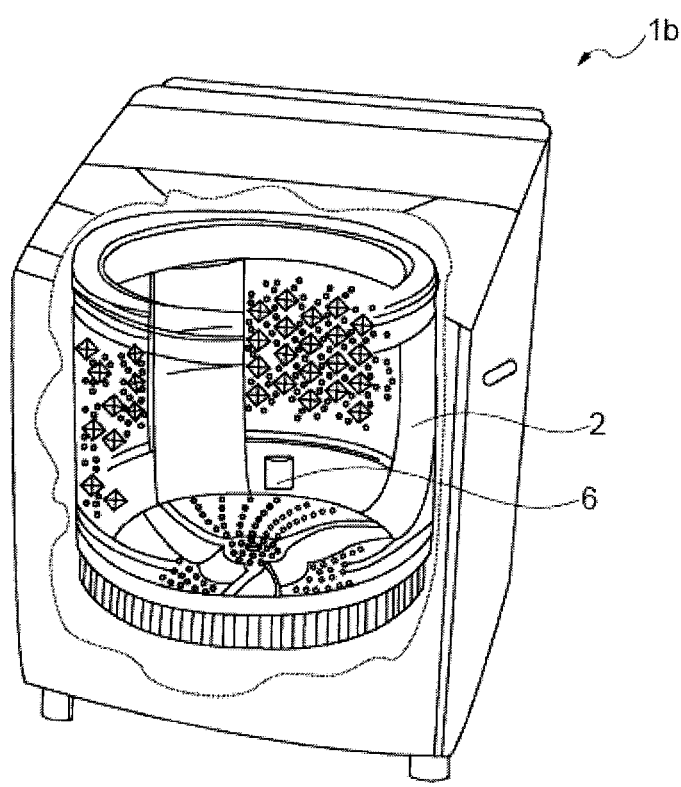

Furthermore, the antimicrobial water unit in a stand type washing machine 1b can be installed, for example, on a backside of a part 6 of the wall surface of the washing tub 2 as shown in FIG. 1(b).

Namely, in the case of filling washing water in the washing tub 2, the washing water is filled to the backside of the wall surface of the washing tub 2, via plural penetration holes that are formed on the wall surface.

Accordingly, as the antimicrobial water unit is installed on the backside of the part 6 of the wall surface of the washing tub 2, the silver ions can be constantly released into washing water which passes through from the backside of the washing tub 2. As a result, it becomes possible to supply efficiently the antimicrobial water to the washing tub 2.

Furthermore, since the washing tub 2 repeats movement in a forward rotational direction and a reverse rotational direction during washing of a subject for washing, when the antimicrobial water unit is installed on the backside of the part 6 of the wall surface of the washing tub 2, the antimicrobial glass is stirred in the washing water so that it becomes possible to supply more efficiently the antimicrobial water to the washing tub 2.

Figure 2A:
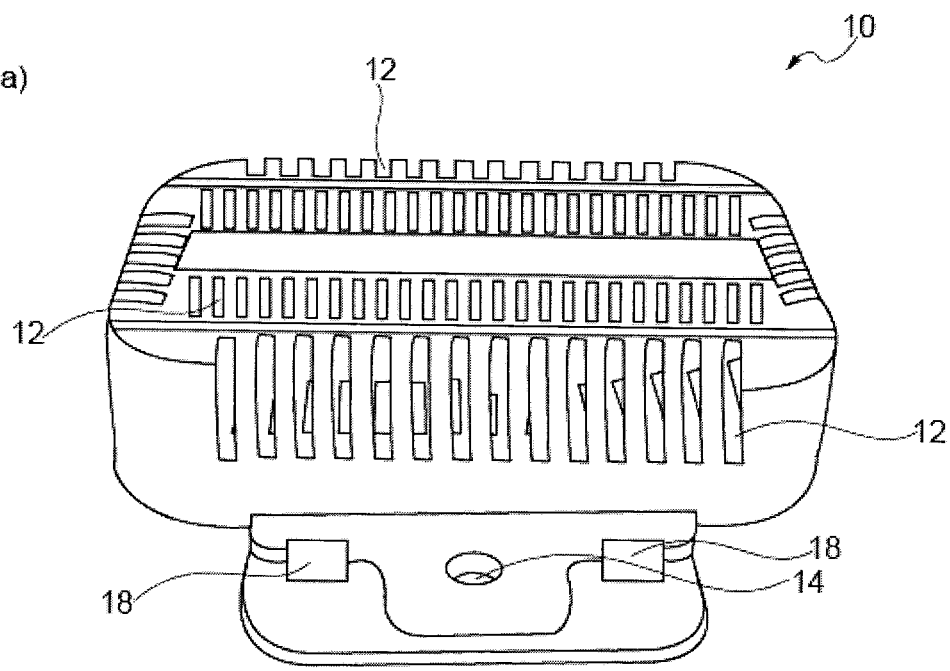
FIG. 2(a) and FIG. 2(b) are drawings which are provided for describing the antimicrobial water unit.
Figure 2B:
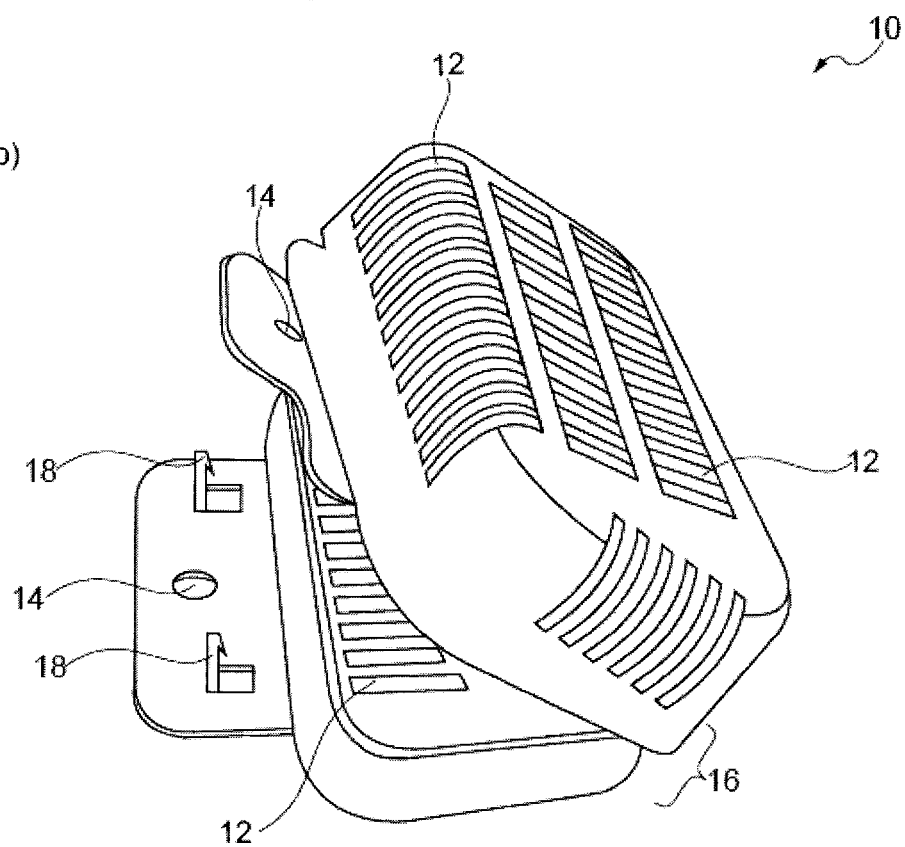

Furthermore, as shown in FIG. 2(*a*) and FIG. 2(*b*), an antimicrobial water unit 10 is preferably a plastic coated member equipped with an opening 12 for pass-through of water and preferably has a fixing hole 14 for fixing onto an inner wall of a circulating water path or a backside of a wall surface of a washing tub by means of a bolt or the like.

Furthermore, it can be preferably open and closed for accommodating the antimicrobial glass inside the unit, and in that case, it is preferably equipped with a hinge part 16 and a lock part 18.

The volume of the antimicrobial water unit 10 is generally 10 to 30 cm$^2$ from the viewpoint of having a space for installation. Within such volume, 10 to 30 g of the antimicrobial glass can be generally accommodated.

Meanwhile, for protecting a subject for washing against microbes and efficiently suppressing an occurrence of black mold or the like in a washing tub, it was confirmed that the silver ion concentration needs to be a value of 1 ppb or more in washing water in the washing tub. It was also confirmed that, to suppress the coloration of a subject for washing, the silver ion concentration needs to be a value of 90 ppb or less in washing water in the washing tub.

It was also confirmed that, when the antimicrobial glass of the present invention is applied to an antimicrobial water unit of a commercially available washing machine, the silver ion concentration in washing water can be stably maintained at a value that is within the aforementioned range.

2. Composition

Regarding the composition of the antimicrobial glass of the present invention, it is characterized in that it contains $Ag_2O$, $P_2O_5$, CaO, ZnO, $K_2O$, $Al_2O_3$, and MgO as a raw material, and when the total amount of the antimicrobial glass is 100% by weight, the content of $Ag_2O$ has a value within the range of above 5% by weight but 10% by weight or less, the content of $P_2O_5$ has a value within the range of 55 to 75% by weight, the content of CaO has a value within the range of 1 to 10% by weight, the content of ZnO has a value of below 10% by weight, the content of $K_2O$ has a value within the range of 5 to 20% by weight, the content of $Al_2O_3$ has a value within the range of 1 to 10% by weight, and the content of MgO has a value within the range of 5 to 20% by weight.

This is because, when the antimicrobial glass has the aforementioned composition, not only the shape and maximum diameter of an antimicrobial glass described below can be obtained but also a certain silver ion elution amount can be maintained over a long period of time even if it is a compact amount.

Hereinbelow, each component is separately and specifically described.

(1) $Ag_2O$ $Ag_2O$ as a raw material is a basic substance of silver ions which are an antimicrobial component released at the time of dissolution of glass components.

Furthermore, the antimicrobial glass of the present invention is characterized in that the content of $Ag_2O$ as a raw material has a value within the range of above 5% by weight but 10% by weight or less.

This is because, when the content of $Ag_2O$ has a value of 5% by weight or less, the silver ion elution amount becomes insufficient to yield a case in which protection of a subject for washing against microbes is insufficient or the occurrence of black mold or the like in a washing tub is not sufficiently suppressed. In addition, when it is desired to increase an absolute amount of an antimicrobial glass to be used for increasing the silver ion elution amount, accommodation in a narrow space in an antimicrobial water unit of a washing machine may be difficult to be achieved. On the other hand, when the content of $Ag_2O$ has a value of above 10% by weight, it may be difficult to homogeneously disperse $Ag_2O$ in an antimicrobial glass so that metal silver is precipitated in the antimicrobial glass or metal silver remains in a crucible during the process of producing an antimicrobial glass, making it difficult to obtain an antimicrobial glass with homogeneous quality.

As such, it is more preferable that the content of $Ag_2O$ as a raw material has a value within the range of 5.5 to 8% by weight. It is even more preferably a value within the range of 6 to 7% by weight.

(2) $P_2O_5$ $P_2O_5$ as a raw material basically functions as an oxide for forming a network, and it also relates to improvement of transparency or the property of homogeneous release of silver ions.

Furthermore, the antimicrobial glass of the present invention is characterized in that the content of $P_2O_5$ as a raw material has a value within the range of 55 to 75% by weight.

This is because, when the content of $P_2O_5$ has a value of below 55% by weight, the solubility of the antimicrobial glass is excessively lowered to yield an insufficient silver ion elution amount, and thus there may be a case in which protection of a subject for washing against microbes is insufficient or the occurrence of black mold or the like in a washing tub is not sufficiently suppressed. In addition, there may be a case in which it is difficult to homogeneously disperse a large amount of $Ag_2O$, that is, above 5% by weight, in the antimicrobial glass during the process of producing an antimicrobial glass. On the other hand, when the content of $P_2O_5$ has a value of above 75% by weight, the solubility of an antimicrobial glass is excessively increased so that not only it is difficult to maintain stably the predetermined silver ion elution amount over a long period of time but also the black coloration of a subject for washing may easily occur due to presence of excessive silver ions.

Meanwhile, it is believed that the black coloration based on the presence of excessive silver ions is caused by decomposition of silver chloride by light such as sunlight, in which the silver chloride has been formed of silver ions and chlorides contained in washing water.

As such, it is more preferable that the content of $P_2O_5$ has a value within the range of 58 to 70% by weight. It is even more preferably a value within the range of 60 to 65% by weight.

(3) CaO

CaO as a raw material basically functions as an oxide for modifying a network, and it also relates to improvement of transparency or control of melting temperature.

Furthermore, the antimicrobial glass of the present invention is characterized in that the content of CaO as a raw material has a value within the range of 1 to 10% by weight.

This is because, when the content of CaO has a value of below 1% by weight, the solubility of the antimicrobial glass is excessively increased so that it is difficult to maintain stably a predetermined silver ion elution amount over a long period of time, and also black coloration of a subject for washing may easily occur due to presence of excessive silver ions. On the other hand, when the content of CaO has a value of above 10% by weight, the solubility of an antimicrobial glass is excessively lowered to yield a case in which protection of a subject for washing against microbes is insufficient or the occurrence of black mold or the like in a washing tub is not sufficiently suppressed.

As such, it is more preferable that the content of CaO has a value within the range of 1.5 to 5% by weight. It is even more preferably a value within the range of 2 to 3% by weight.

(4) ZnO

ZnO as a raw material is basically a substance for maintaining stably the flexibility of an antimicrobial glass even if the temperature changes.

Furthermore, the antimicrobial glass of the present invention is characterized in that the content of ZnO as a raw material has a value of below 10% by weight, that is, a value of below 0 to 10% by weight (with the proviso that, 0% is excluded), or 0% by weight.

This is because, when the content of ZnO has a value of 10% by weight or more, the solubility of the antimicrobial glass is excessively increased so that it is difficult to maintain stably a predetermined silver ion elution amount over a long period of time, and also black coloration of a subject for washing may easily occur due to presence of excessive silver ions. On the other hand, when the content of ZnO is excessively low, the solubility of an antimicrobial glass can be slightly lowered so that the antimicrobial property may be impaired.

As such, it is more preferable that the content of ZnO has a value within the range of 4 to 9.5% by weight. It is even more preferably a value within the range of 8 to 9.1% by weight.

Figure 3:
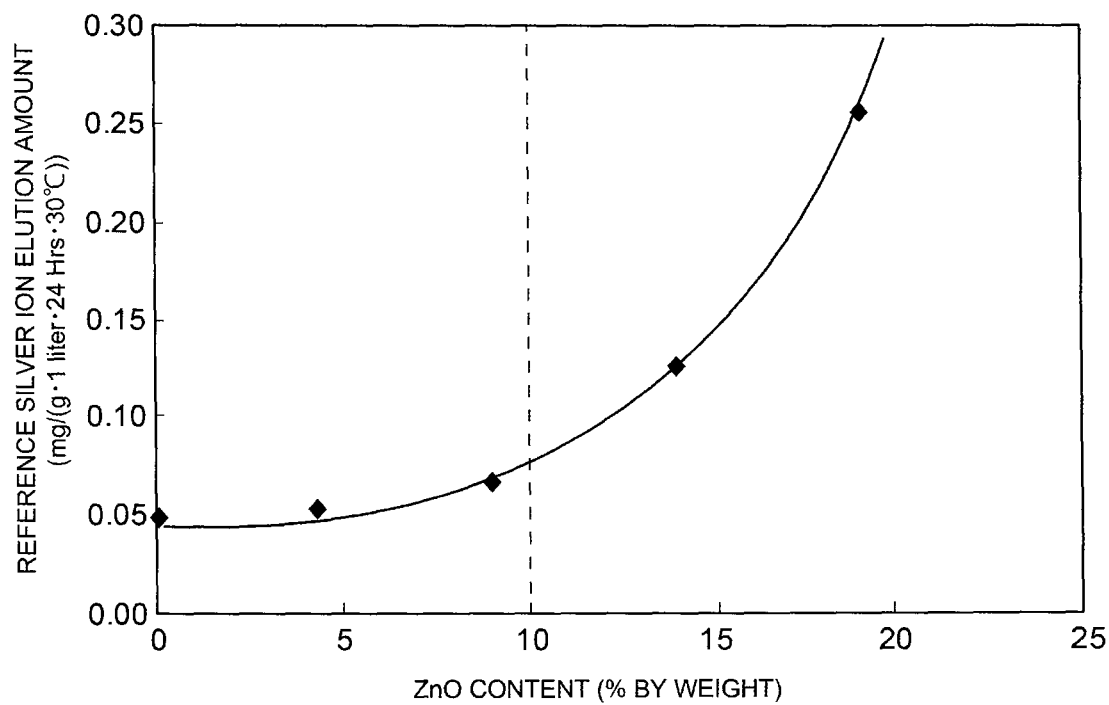
FIG. 3 is a drawing provided for describing the relationship between the ZnO content and a reference silver ion elution amount.
Figure 4:
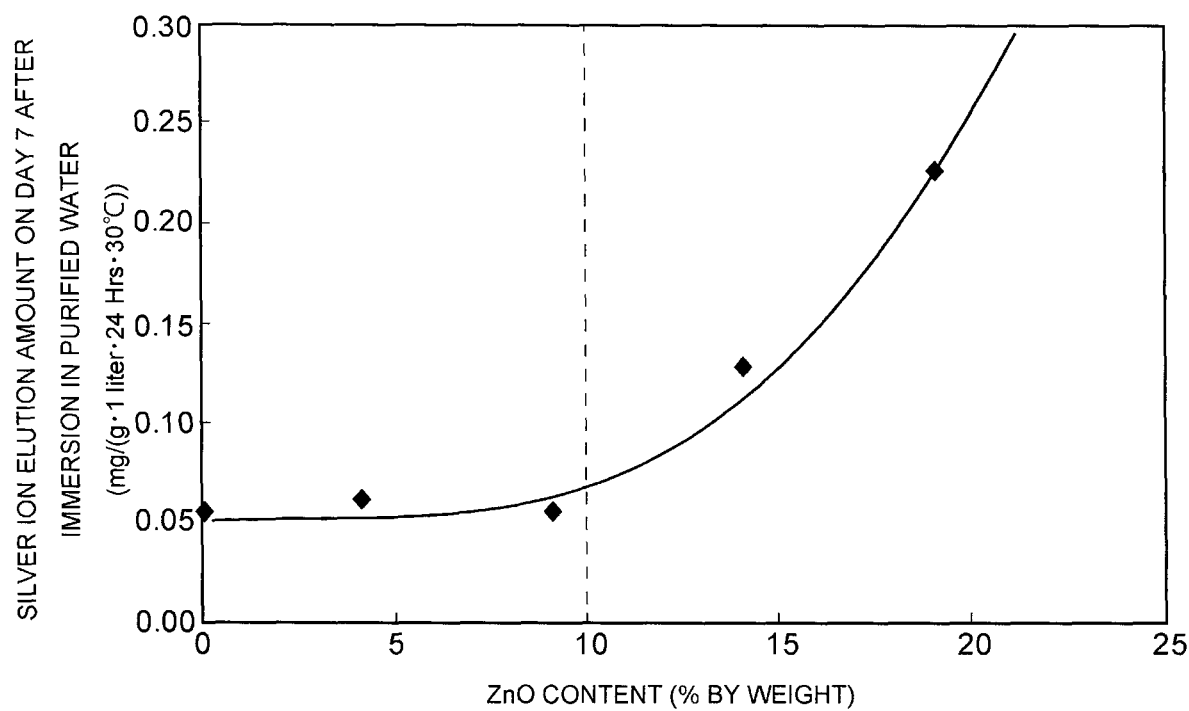
FIG. 4 is a drawing provided for describing the relationship between the ZnO content and a silver ion elution amount on Day 7 after immersion in purified water.
Figure 5:
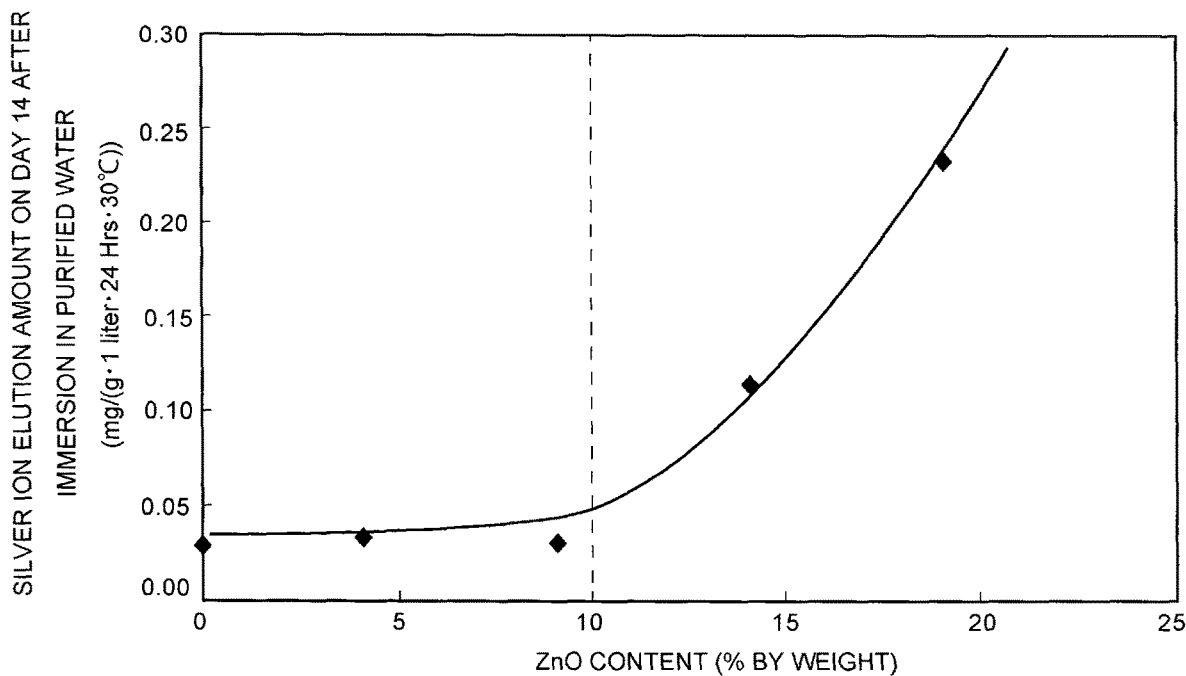
FIG. 5 is a drawing provided for describing the relationship between the ZnO content and a silver ion elution amount on Day 14 after immersion in purified water.

Herein, by using FIGS. 3 to 5, the relationship between the ZnO content and silver ion elution amount is described.

First, in FIG. 3, a characteristics curve in which the ZnO content (% by weight) is plotted against the horizontal axis when the total amount of the raw material of an antimicrobial glass is 100% by weight and the reference silver ion elution amount (mg/(g·1 liter·24 Hrs·30° C.)) is plotted against the vertical axis is shown.

Meanwhile, the reference silver ion elution amount indicates a silver ion elution amount which is measured after immersing 30 g of the antimicrobial glass as a subject for measurement in 1 liter of purified water (30° C., pH 6.5) and keeping it in a closed system for 24 hours with the temperature maintained.

Furthermore, as for the antimicrobial glass as a subject for measurement, those produced in Examples 1 to 3 and Comparative Examples 1 and 2 described below are used.

Namely, the antimicrobial glass in which the contents of $Ag_2O$ and CoO are not modified while the content of ZnO is modified with modification of other components at the same ratio as the change in ZnO content is used.

As it is understood from the characteristics curve, it is found that the silver ion elution amount (mg/(g·1 liter·24 Hrs·30° C.)) increases in accordance with an increase in the ZnO content (% by weight).

More specifically, within a range in which the ZnO content is a value within the range of below 10% by weight, it is found that the reference silver ion elution amount stably maintains a value of approximately 0.05 mg/(g·1 liter·24 Hrs·30° C.), but when the ZnO content is 10% by weight or more, the reference silver ion elution amount starts to increase rapidly, that is, when the ZnO content is 14.05% by weight, it is increased to 0.1245 mg/(g·1 liter·24 Hrs·30° C.), and when the ZnO content is 19.05% by weight, it is increased up to 0.255 mg/(g·1 liter·24 Hrs·30° C.)

Furthermore, when the reference silver ion concentration of the antimicrobial glass has a value of above 0.1 mg/(g·1 liter·24 Hrs·30° C.), it is found that the black coloration of a subject for washing easily occurs when applied to an antimicrobial water unit of a commercially available washing machine.

Thus, based on the characteristics curve shown in FIG. 3, it is understood that, from the viewpoint of suppressing coloration of a subject for washing, it is necessary that the content of ZnO as a raw material is adjusted to a value of below 10% by weight.

It is also understood that, as the content of ZnO has a value of below 10% by weight, a constant silver ion elution amount can be stably maintained even when a deviation in the ZnO content occurs during the process of producing an antimicrobial glass, for example.

Furthermore, in FIG. 4, a characteristics curve in which the ZnO content (% by weight) is plotted against the horizontal axis when the total amount of the raw material of an antimicrobial glass is 100% by weight and the silver ion elution amount (mg/(g·1 liter·24 Hrs·30° C.)) on Day 7 after immersion in purified water is plotted against the vertical axis is shown.

Herein, the silver elution amount on Day 7 after immersion in purified water is measured as described below.

Namely, after measuring the aforementioned reference silver ion elution amount, 1 liter of the purified water containing eluted silver ions is discarded, the antimicrobial glass remained after dissolving is immersed in 1 liter of fresh purified water, and the antimicrobial glass is immersed and kept for 5 days in purified water at the same conditions as the conditions for measuring the reference silver ion elution amount.

Subsequently, 1 liter of the purified water containing eluted silver ions is discarded, the antimicrobial glass remained after dissolving is immersed in 1 liter of fresh purified water and kept for 24 hours at the same conditions as the conditions for measuring the reference silver ion elution amount. After that, the silver ion elution amount is measured and the result is used as a silver ion elution amount on Day 7 after immersion in purified water.

Furthermore, in FIG. 5, a characteristics curve in which the ZnO content (% by weight) is plotted against the horizontal axis when the total amount of the raw material of an antimicrobial glass is 100% by weight and the silver ion elution amount (mg/(g·1 liter·24 Hrs·30° C.)) on Day 14 after immersion in purified water is plotted against the vertical axis is shown.

Herein, the silver elution amount on Day 14 after immersion in purified water is measured as described below.

Namely, after measuring the aforementioned silver ion elution amount on Day 7 after immersion in purified water, 1 liter of the purified water containing eluted silver ions is discarded, the antimicrobial glass remained after dissolving is immersed in 1 liter of fresh purified water and kept for 6 days at the same conditions as the conditions for measuring the reference silver ion elution amount.

Subsequently, 1 liter of the purified water containing eluted silver ions is discarded, the antimicrobial glass remained after dissolving is immersed in 1 liter of fresh purified water and kept for 24 hours at the same conditions as the conditions for measuring the reference silver ion elution amount. After that, the silver ion elution amount is measured and the result is used as a silver ion elution amount on Day 14 after immersion in purified water.

As it is understood from those characteristics curves, it is found that, when the ZnO content has a value of 10% by weight or more, the silver ion elution amount increases rapidly even on Day 7 or Day 14 after immersion in purified water, similar to Day 1 after immersion in purified water (reference silver ion elution amount).

As such, based on the characteristics curves shown in FIGS. 4 and 5, it is understood that, from the viewpoint of suppressing coloration of a subject for washing not only at an early stage but also over a long period of time, the content of ZnO as a raw material is required to have a value of below 10% by weight.

Figure 6:
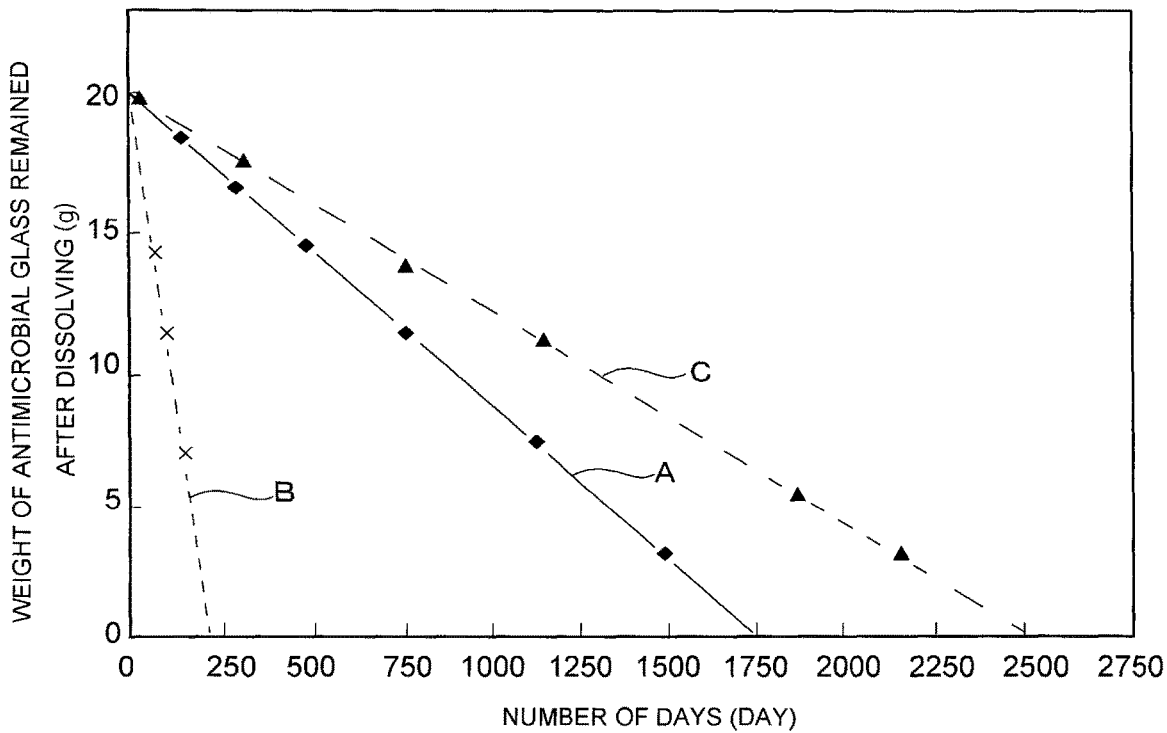
FIG. 6 is a drawing provided for describing the relationship between the ZnO content and the dissolution speed of an antimicrobial glass over a long period of time.

Next, by using FIG. 6, the relationship between the ZnO content and the dissolution speed of an antimicrobial glass over a long period of time is described.

Specifically, in FIG. 6, a characteristics curve in which the number of days (day) for immersing the antimicrobial glass in purified water is plotted against the horizontal axis and the weight (g) of the antimicrobial glass remained after dissolving is plotted against the vertical axis is shown.

In addition, the characteristics curve A is a characteristics curve having, as a subject for measurement, the antimicrobial glass which has been produced in Example 1 described below (ZnO content: 9.05% by weight, $Ag_2O$ content: 6% by weight), the characteristics curve B is a characteristics curve having, as a subject for measurement, the antimicrobial glass which has been produced in Comparative Example 3 described below (ZnO content: 13.8% by weight, $Ag_2O$ content: 6% by weight), and the characteristics curve C is a characteristics curve having, as a subject for measurement, the antimicrobial glass which has been produced in Comparative Example 4 described below (ZnO content: 0% by weight, $Ag_2O$ content: 3.04% by weight).

Meanwhile, the weight of the antimicrobial glass remained after dissolving is measured according to the basically the same method as the aforementioned method for measuring the reference silver ion elution amount, the silver ion elution amount on Day 7 after immersion in purified water, and the silver ion elution amount on Day 14 after immersion in purified water except that the use amount of an antimicrobial glass was 20 g instead of 30 g.

Namely, for a case in which the weight of an antimicrobial glass on Day 7 after immersion in purified water is measured after measuring the weight of an antimicrobial glass on Day 1 after immersion in purified water, the weight of an antimicrobial glass on Day 1 after immersion in purified water is measured first, 1 liter of the purified water containing eluted silver ions is discarded, the antimicrobial glass remained after dissolving is immersed in 1 liter of fresh purified water, and kept for 6 days at the same conditions as the conditions for measuring the reference silver ion elution amount.

Subsequently, the weight of the antimicrobial glass remained after dissolving is measured and the result is used as the weight (g) of an antimicrobial glass on Day 7 after immersion in purified water.

In addition, the process including discarding 1 liter of the purified water containing eluted silver ions, immersing the antimicrobial glass remained after dissolving in 1 liter of fresh purified water, and keeping it until the next measurement day is repeated.

Meanwhile, the weight of the antimicrobial glass remained after dissolving is measured on Day 1, Day 7, Day 14, Day 30, . . . , and Day 2555, and the measurement is terminated when the antimicrobial glass is completely dissolved.

First, as it is understood from those characteristics curves A and C, it is found that, for an antimicrobial glass with the ZnO content of below 10% by weight, it takes 2000 days or so for 20 g of the antimicrobial glass to dissolve completely, and thus it can elute silver ions very stably over a long period of time.

Meanwhile, as it is understood from the characteristics curve B, it is found that, when the ZnO content is a value of 10% by weight or more, the time to have complete dissolution of 20 g of the antimicrobial glass is significantly shortened, that is, 250 days or so, and thus it is difficult to have stable elution of silver ions over a long period of time.

As such, from the viewpoint of maintaining stably a predetermined silver ion elution amount over a long period of time, it is understood that the content of ZnO as a raw material needs to have a value of below 10% by weight.

Figure 7:
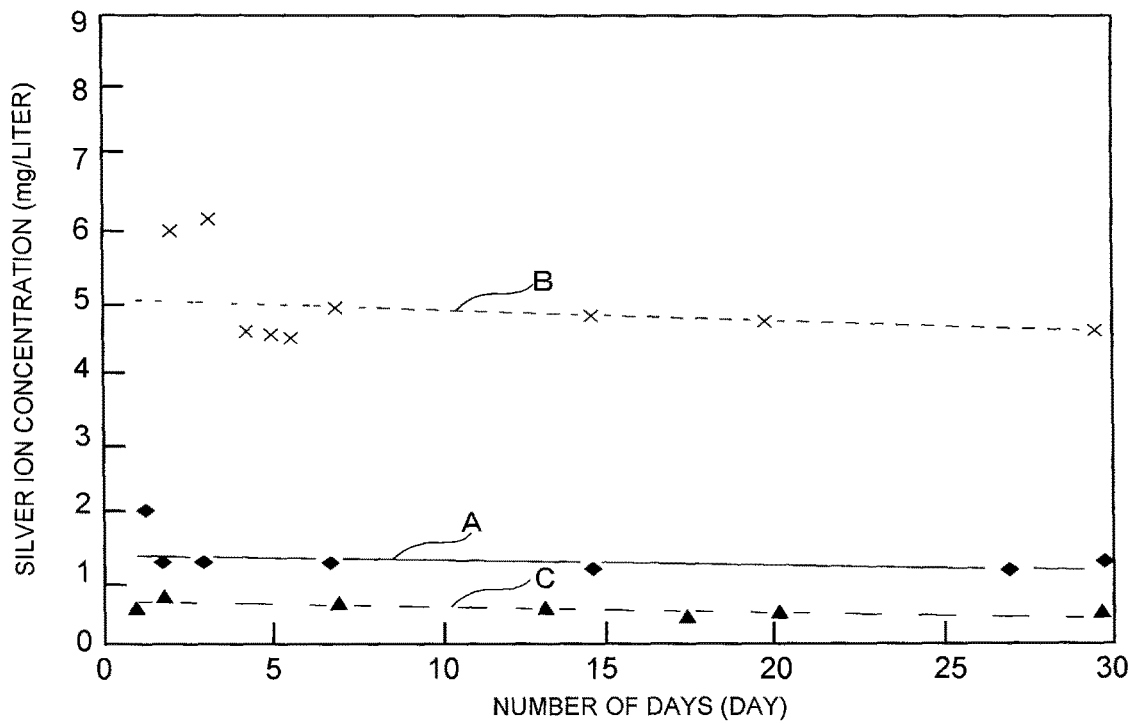
FIG. 7 is a drawing provided for describing the relationship between the contents of ZnO and $Ag_2O$ and the silver ion concentration.

Furthermore, by using FIG. 7, the relationship between the ZnO and $Ag_2O$ content and silver ion concentration is described.

Specifically, in FIG. 7, a characteristics curve in which number of days (day) for immersing the antimicrobial glass in purified water is plotted against the horizontal axis and the silver ion concentration (mg/liter) in purified water in which the antimicrobial glass is immersed is plotted against the vertical axis is shown.

In addition, the characteristics curve A is a characteristics curve having, as a subject for measurement, the antimicrobial glass which has been produced in Example 1 described below (ZnO content: 9.05% by weight, $Ag_2O$ content: 6% by weight), the characteristics curve B is a characteristics curve having, as a subject for measurement, the antimicrobial glass which has been produced in Comparative Example 3 (ZnO content: 13.8% by weight, $Ag_2O$ content: 6% by weight), and the characteristics curve C is a characteristics curve having, as a subject for measurement, the antimicrobial glass which has been produced in Comparative Example 4 (ZnO content: 0% by weight, $Ag_2O$ content: 3.04% by weight).

Meanwhile, the silver ion concentration in purified water is measured according to the basically the same method as the aforementioned method for measuring the reference silver ion elution amount, the silver ion elution amount on Day 7 after immersion in purified water, and the silver ion elution amount on Day 14 after immersion in purified water except that the use amount of an antimicrobial glass was 20 g instead of 30 g.

Namely, for a case in which the silver ion concentration on Day 7 after immersion in purified water is measured after measuring the silver ion concentration on Day 1 after immersion in purified water, the silver ion concentration on Day 1 after immersion in purified water is measured first, 1 liter of the purified water containing eluted silver ions is discarded, the antimicrobial glass remained after dissolving is immersed in 1 liter of fresh purified water, and kept for 5 days in purified water at the same conditions as the conditions for measuring the reference silver ion elution amount.

Subsequently, 1 liter of the purified water containing eluted silver ions is discarded, the antimicrobial glass remained after dissolving is immersed in 1 liter of fresh purified water, and after allowing it to stand for 24 hours at the same conditions as the conditions for measuring the reference silver ion elution amount, the silver ion concentration is measured and the result is used as the silver ion concentration (mg/liter) on Day 7 after immersion in purified water.

In addition, the process of keeping it until the next measurement day is repeated.

Meanwhile, the silver ion concentration is measured on Day 1, Day 7, Day 14, Day 30, . . . , and Day 2555.

First, as it is understood from the characteristics curve A, it is found that, for an antimicrobial glass with the ZnO content of below 10% by weight and the $Ag_2O$ content of above 5% by weight, the silver ion concentration of 1 to 2 mg/liter or so can be stably maintained for at least 30 days even when the purified water is exchanged during the process.

Accordingly, the subject for washing can be effectively protected against microbes and an occurrence of black coloration of the subject for washing can be effectively suppressed while an occurrence of black mold or the like in a washing tub is effectively suppressed.

Meanwhile, as it is understood from the characteristics curve B, it is found that, for an antimicrobial glass with the ZnO content of 10% by weight or more and the $Ag_2O$ content of above 5% by weight, the silver ion concentration can be maintained at constant level, but as the silver ion concentration is very high like 5 mg/liter or so, black coloration of the subject for washing may easily occur when it is applied to an antimicrobial water unit of a commercially available washing machine.

Furthermore, as it is understood from the characteristics curve C, it is found that, for an antimicrobial glass with the ZnO content of below 10% by weight and the $Ag_2O$ content of 5% by weight or less, the silver ion concentration can be maintained at constant level, but as the silver ion concentration is very low like 0.5 mg/liter or so, it is difficult to have effective protection of a subject for washing against microbes and effective suppression of an occurrence of black mold or the like in a washing tub when applied to an antimicrobial water unit of a commercially available washing machine.

Accordingly, from the viewpoint of having effective suppression of an occurrence of black mold or the like in a washing tub and effective protection of a subject for washing against microbes while suppressing coloration of a subject for washing, it is understood that the content of ZnO as a raw material needs to have a value of below 10% by weight and also the content of $Ag_2O$ needs to have a value of above 5% by weight.

(5) $K_2O$ $K_2O$ as a raw material basically functions as an oxide for modifying a network, and it also relates to improvement of transparency or control of melting temperature.

Furthermore, the antimicrobial glass of the present invention is characterized in that the content of $K_2O$ as a raw material has a value within the range of 5 to 20% by weight.

This is because, when the content of $K_2O$ has a value of below 5% by weight, the solubility of the antimicrobial glass is excessively lowered so that the silver ion elution amount becomes insufficient to yield insufficient protection of a subject for washing against microbes or the occurrence of black mold or the like in a washing tub is not sufficiently suppressed. On the other hand, when the content of $K_2O$ is a value of above 20% by weight, the solubility of the antimicrobial glass is excessively increased, and thus it becomes difficult to maintain a predetermined silver ion elution amount over a long period of time and black coloration of a subject for washing may easily occur due to excessive silver ions.

As such, it is more preferable that the content of $K_2O$ has a value within the range of 6 to 15% by weight. It is even more preferably a value within the range of 7 to 9% by weight.

(6) $Al_2O_3$ $Al_2O_3$ as a raw material basically functions to enhance the chemical durability of an antimicrobial glass, and it is a substance also related to suppressing devitrification.

Furthermore, the antimicrobial glass of the present invention is characterized in that the content of $Al_2O_3$ as a raw material has a value within the range of 1 to 10% by weight.

This is because, when the content of $Al_2O_3$ has a value of below 1% by weight, the solubility of the antimicrobial glass is excessively increased so that it becomes difficult to maintain a predetermined silver ion elution amount over a long period of time and black coloration of a subject for washing may easily occur due to excessive silver ions. On the other hand, when the content of $Al_2O_3$ has a value of above 10% by weight, the solubility of an antimicrobial glass is excessively lowered, and thus the silver ion elution amount becomes insufficient to yield insufficient protection of a subject for washing against microbes or the occurrence of black mold or the like in a washing tub is not sufficiently suppressed.

As such, it is more preferable that the content of $Al_2O_3$ has a value within the range of 2 to 8% by weight. It is even more preferably a value within the range of 3 to 5% by weight.

Furthermore, it is preferable that, when the content of ZnO is C1 (% by weight) and the content of $Al_2O_3$ is C2 (% by weight), C2/C1 preferably has a value of 0.4 or more.

This is because, when the ratio between the content of ZnO and the content of $Al_2O_3$ has such value, a predetermined silver ion elution amount can be more stably maintained.

Namely, because ZnO as a raw material of the antimicrobial glass of the present invention is a substance having an influence of greatly increasing the solubility of the antimicrobial glass while $Al_2O_3$ is a substance having an influence of greatly decreasing the solubility of the antimicrobial glass, the ratio between these raw materials has a strong relationship with the solubility of an antimicrobial glass to be obtained.

More specifically, when C2/C1 has a value of below 0.4, the solubility of an antimicrobial glass increases excessively so that it becomes difficult to maintain stably a predetermined silver ion elution amount over a long period of time and black coloration of a subject for washing may easily occur due to excessive silver ions. On the other hand, when C2/C1 has an excessively high value, the solubility of an antimicrobial glass can be easily decreased to a slightly lower value, and thus the antimicrobial property may be impaired.

As such, it is preferable that, when the content of ZnO is C1 (% by weight) and the content of $Al_2O_3$ is C2 (% by weight), C2/C1 more preferably has a value within the range of 0.42 to 1.5. It even more preferably has a value within the range of 0.43 to 1.

Figure 8:
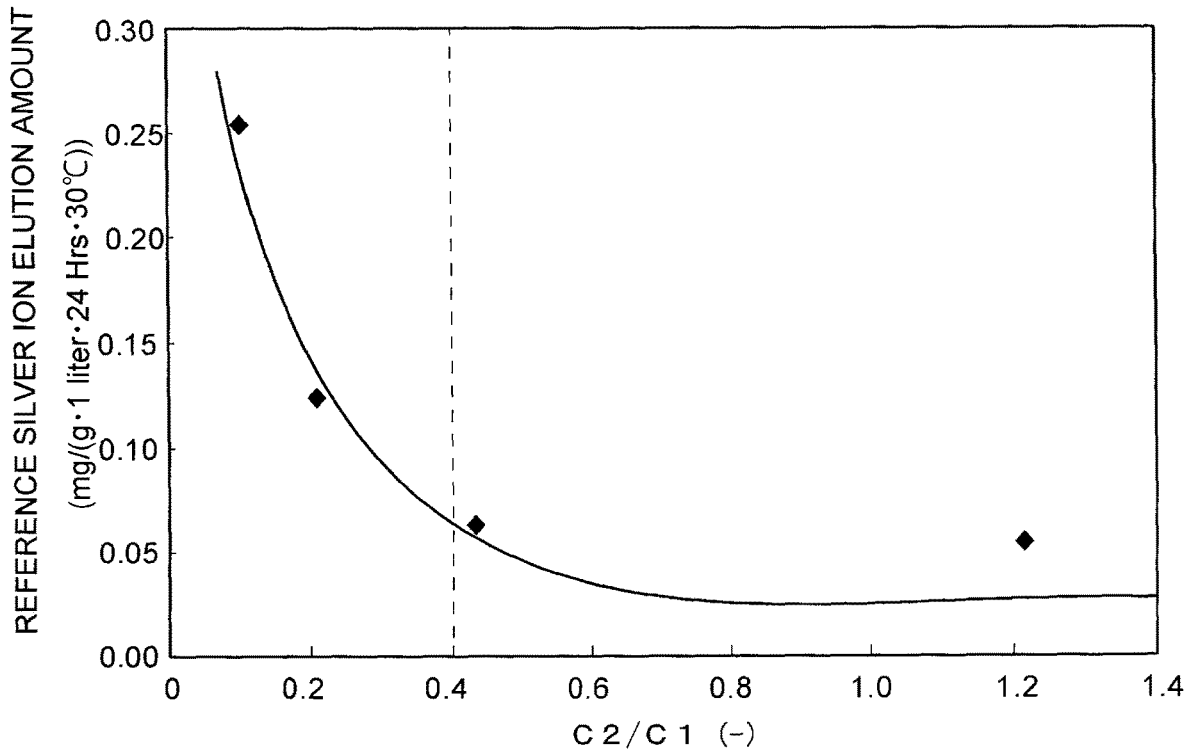
FIG. 8 is a drawing provided for describing the relationship between the value of C2/C1 and a reference silver ion elution amount.
Figure 9:
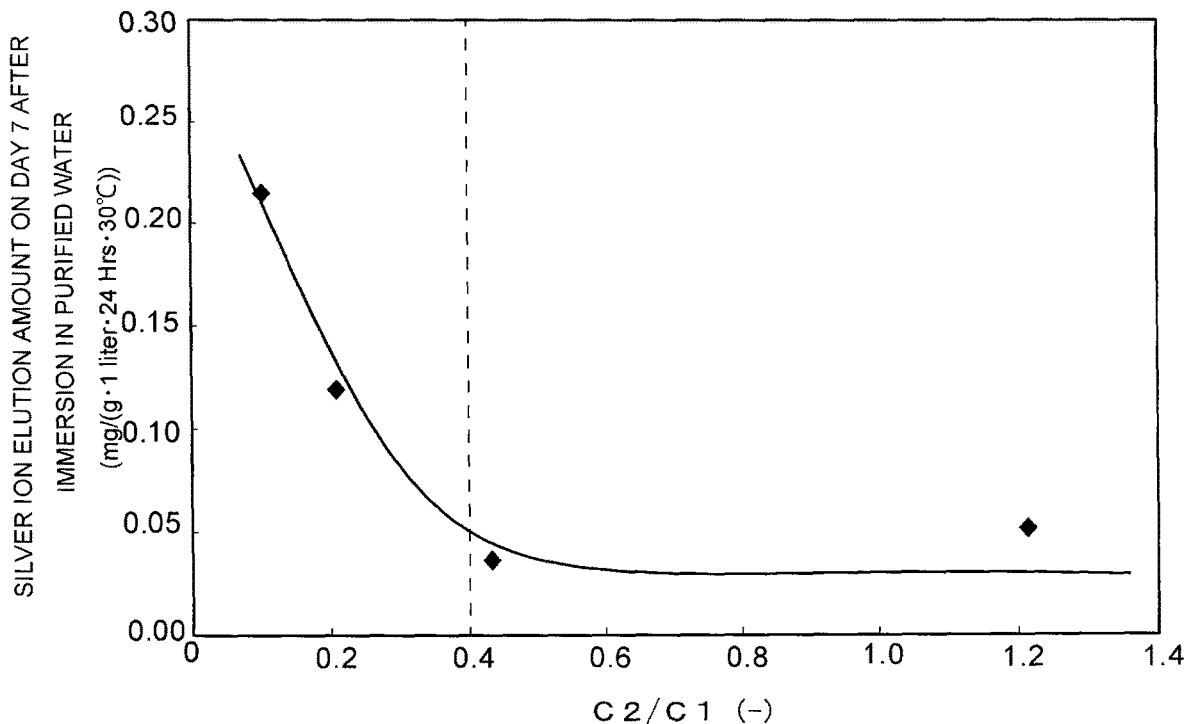
FIG. 9 is a drawing provided for describing the relationship between the value of C2/C1 and a silver ion elution amount on Day 7 after immersion.
Figure 10:
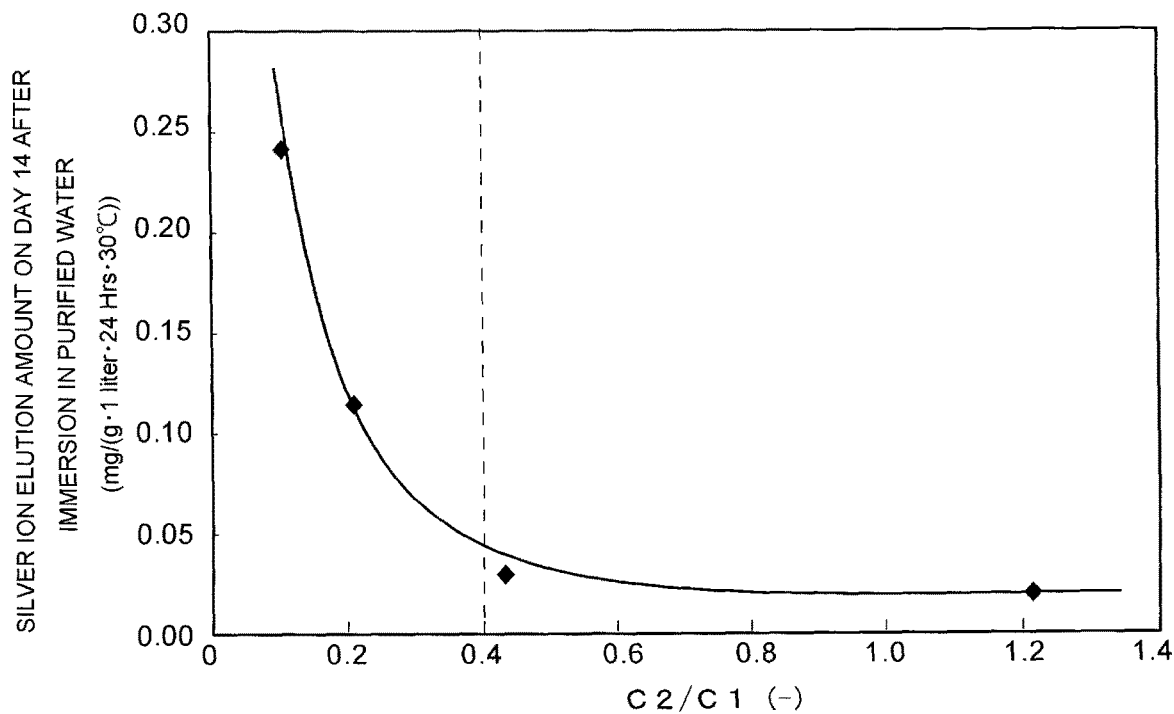
FIG. 10 is a drawing provided for describing the relationship between the value of C2/C1 and a silver ion elution amount on Day 14 after immersion.

Herein, by using FIGS. 8 to 10, the relationship between the value of C2/C1 and a reference silver ion elution amount is described.

First, in FIG. 8, a characteristics curve in which the C2/C1 (–) is plotted against the horizontal axis and the reference silver ion elution amount (mg/(g·1 liter·24 Hrs·30° C.)) is plotted against the vertical axis is shown.

Furthermore, as for the antimicrobial glass as a subject for measurement, those produced in the Examples 1 to 3 and Comparative Examples 1 and 2 described below were used.

Namely, the antimicrobial glass in which the contents of $Ag_2O$ and CoO are not modified while the content of ZnO is modified with modification of other components at the same ratio as the change in ZnO content is used.

As it is understood from the characteristics curve, it is found that the silver ion elution amount mg/(g·1 liter·24 Hrs·30° C.) decreases in accordance with an increase in C2/C1 (−).

More specifically, within the range in which C2/C1 is below 0.4, the silver ion elution amount rapidly decreases in accordance with an increase in C2/C1, that is, it is 0.255 mg/(g·1 liter·24 Hrs·30° C.) when C2/C1 is 0.101 but it is decreased to 0.1245 mg/(g·1 liter·24 Hrs·30° C.) when C2/C1 is 0.208. When C2/C1 is 0.433, it is further decreased to 0.063 mg/(g·1 liter·24 Hrs·30° C.)

Meanwhile, within the range in which C2/C1 is 0.4 or more, the value of 0.05 mg/(g·1 liter·24 Hrs·30° C.) or so is stably maintained regardless of the C2/C1 value.

Furthermore, when the reference silver ion elution amount of an antimicrobial glass has a value of 0.1 mg/(g·1 liter·24 Hrs·30° C.) or more, it was confirmed that the black coloration of a subject for washing easily occurs when it is applied to an antimicrobial water unit of a commercially available washing machine.

As such, from the characteristics curve shown in FIG. 8, it is understood that the C2/C1 is preferably adjusted to have a value of 0.4 or less from the viewpoint of suppressing coloration of a subject for washing.

Furthermore, in FIG. 9, a characteristics curve in which the C2/C1 (−) is plotted against the horizontal axis and the silver ion elution amount (mg/(g·1 liter·24 Hrs·30° C.)) based on 7 Days' immersion in purified water is plotted against the vertical axis is shown.

Furthermore, in FIG. 10, a characteristics curve in which the C2/C1 (−) is plotted against the horizontal axis and the silver ion elution amount (mg/(g·1 liter·24 Hrs·30° C.) based on 14 Days' immersion in purified water is plotted against the vertical axis is shown.

As it is understood from those characteristics curves, it is found that, even on Day 7 and Day 14 after immersion in purified water, the silver ion elution amount rapidly decreases within the range in which C2/C1 is less than 0.4, similar to the Day 1 after immersion in purified water (reference silver ion elution amount).

As such, based on the characteristics curves shown in FIGS. 9 and 10, it is understood that, from the viewpoint of suppressing coloration of a subject for washing not only at an early stage but also over a long period of time, the C2/C1 is preferably adjusted to a value of 0.4 or more.

(7) MgO

MgO as a raw material basically functions as an oxide for forming a network, and it also relates to improvement of transparency or control of melting temperature.

Furthermore, the antimicrobial glass of the present invention is characterized in that the content of MgO as a raw material has a value within the range of 5 to 20% by weight.

This is because, when the content of MgO has a value of below 5% by weight, the solubility of the antimicrobial glass is excessively increased, and thus it becomes difficult to maintain stably a predetermined silver ion elution amount over a long period of time and black coloration of a subject for washing may easily occur due to excessive silver ions. On the other hand, when the content of MgO has a value of above 20% by weight, the solubility of an antimicrobial glass is excessively decreased so that the silver ion elution amount becomes insufficient to yield insufficient protection of a subject for washing against microbes or the occurrence of black mold or the like in a washing tub is not sufficiently suppressed.

As such, it is more preferable that the content of MgO has a value within the range of 6 to 15% by weight. It is even more preferably a value within the range of 7 to 9% by weight.

(8) Other Components

Furthermore, when the total amount of the raw materials is less than 100% by weight, it is preferable to contain, as a residual component, other glass components (alkali metal oxide, alkali earth metal oxide, $CeO_2$, CoO, or the like) within the range of 0.05 to 50% by weight.

3. Shape

The antimicrobial glass is also characterized in that it has a tablet shape with a maximum diameter value within the range of 5 to 20 mm.

This is because, as the antimicrobial glass has a shape with a maximum diameter as described above, a predetermined elution amount of silver ions can be stably maintained, together with the aforementioned composition of an antimicrobial glass, over a long period of time even if it is a compact amount.

Specifically, as the antimicrobial glass has a tablet shape, the surface area of an antimicrobial glass can be easily controlled, and also the silver ion elution amount can be more easily controlled.

Furthermore, with a tablet shape, binding between antimicrobial glasses can be also effectively prevented.

Figure 11:
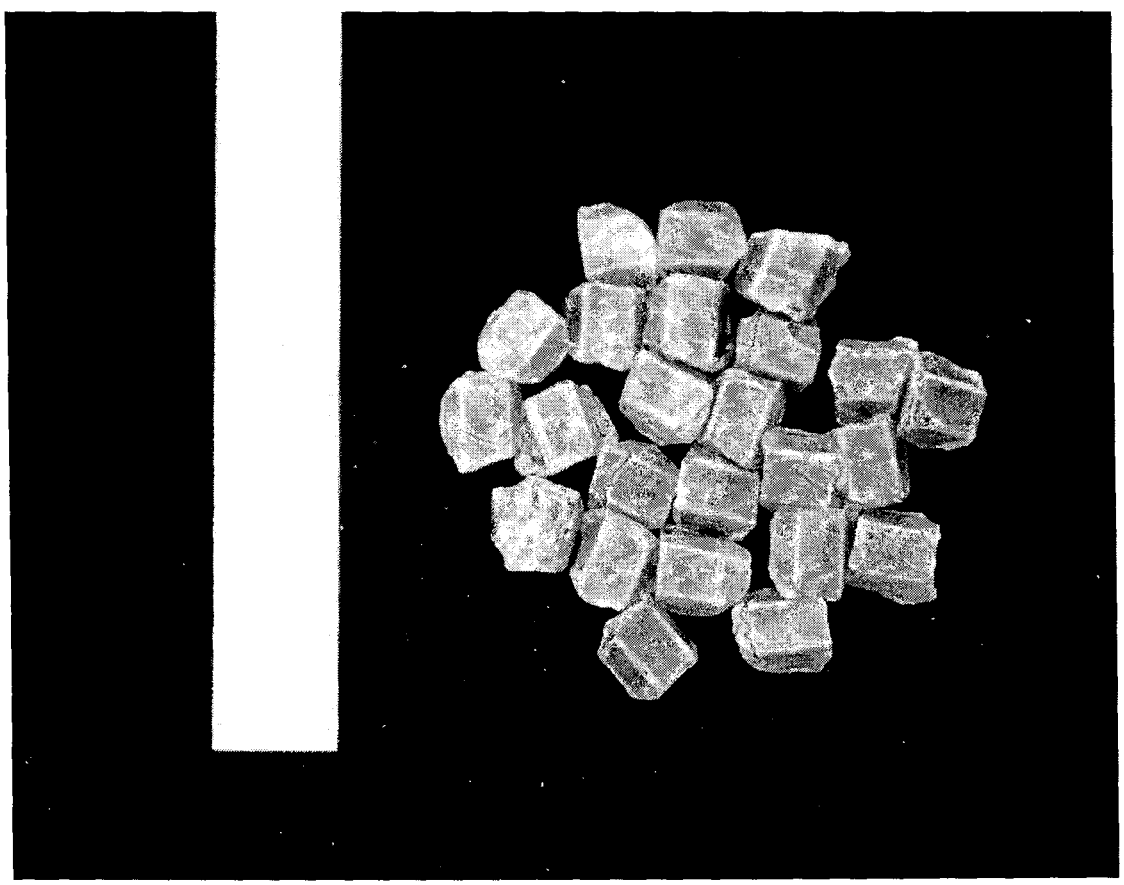
FIG. 11 is a photographic image provided for describing the shape of an antimicrobial glass.

More specific examples include an antimicrobial glass having a trapezoidal crossed hexahedral shape as shown in FIG. 11, but it can be also a so-called tablet shape like rectangular or columnar shape.

It is also preferable that chamfering is performed along the sides of an antimicrobial glass.

This is because, by having this shape, the molding property or polishing property can be also improved.

Furthermore, an antimicrobial glass with such shape can be easily handled or replaced and also loss or breaking caused by water flow can be effectively prevented even when a relatively strong water flow is used.

Furthermore, if the maximum diameter of an antimicrobial glass has a value of below 5 mm, when it is accommodated in an antimicrobial water unit and brought into direct contact with water, it can flow by water pressure so that it can be easily lost together with water flow, or there can be a case in which the specific surface area becomes excessively large so that a predetermined silver ion elution amount may not be stably maintained over a long period of time. Further, it can be easily aggregated during storage. On the other hand, when the maximum diameter of an antimicrobial glass has a value of above 20 mm, it may be difficult to accommodate it in an antimicrobial water unit or to have stable production due to easy occurrence of cracks, and there can be a case in which the specific surface area becomes excessively small so that it becomes difficult to obtain a sufficient silver ion elution amount.

As such, it is more preferable that the maximum diameter of an antimicrobial glass has a value within the range of 7 to 15 mm, and even more preferably a value within the range of 9 to 12 mm.

Meanwhile, the maximum diameter of an antimicrobial glass means a diameter of a sphere circumscribing the antimicrobial glass.

Furthermore, the maximum diameter of an antimicrobial glass can be easily measured by using an optical microscopic image or a nonius.

4. Specific Surface Area

The antimicrobial glass preferably has a specific surface area value within the range of 0.1 to 5 $cm^2/g$.

This is because, by having the specific surface area of an antimicrobial glass in the aforementioned range, a predetermined silver ion elution amount can be more stably maintained over a long period of time.

Namely, when the antimicrobial glass preferably has a specific surface area value of below 0.1 cm²/g, the dissolution speed of an antimicrobial glass is lowered to yield an insufficient silver ion elution amount, and thus protection of a subject for washing against microbes becomes insufficient or an occurrence of black mold or the like in a washing tub may not be sufficiently suppressed. On the other hand, when the antimicrobial glass preferably has a specific surface area value of above 5 cm²/g, the solubility of an antimicrobial glass is increased to yield an excessive silver ion elution amount, and thus it becomes difficult to maintain stably a predetermined silver ion elution amount over a long period of time. Further, the black coloration of a subject for washing caused by excessive silver ions may easily occur.

As such, it is more preferable that the specific surface area of an antimicrobial glass is a value within the range of 1.5 to 8 cm²/g, and even more preferably a value within the range of 2 to 5 cm²/g.

5. Reference Silver Ion Elution Amount

The antimicrobial glass of the present invention preferably has a silver ion elution amount value, that is, reference silver ion elution amount, within the range of 0.025 to 0.1 mg/(g·1 liter·24 Hrs·30° C.), which is measured by, after immersing 30 g of the antimicrobial glass as a subject for measurement in 1 liter of purified water (30° C., pH 6.5), performing the measurement after keeping it in a closed system for 24 hours with the temperature maintained.

This is because, by having the reference silver ion elution amount of an antimicrobial glass in the aforementioned range, a predetermined silver ion elution amount can be more stably maintained over a long period of time.

Namely, when the reference silver ion elution amount has a value of below 0.025 mg/(g·1 liter·24 Hrs·30° C.), protection of a subject for washing against microbes becomes insufficient or an occurrence of black mold or the like in a washing tub may not be sufficiently suppressed. On the other hand, when the reference silver ion elution amount has a value of above 0.1 mg/(g·1 liter·24 Hrs·30° C.), it becomes difficult to maintain stably a predetermined silver ion elution amount over a long period of time and also black coloration of a subject for washing caused by excessive silver ions may easily occur.

As such, it is more preferable that the reference silver ion elution amount of an antimicrobial glass is a value within the range of 0.04 to 0.08 mg/(g·1 liter·24 Hrs·30° C.), and even more preferably a value within the range of 0.06 to 0.07 mg/(g·1 liter·24 Hrs·30° C.)

6. Coated Member

The antimicrobial glass of the present invention is preferably accommodated inside a coated member which is provided with an opening for passing water therethrough, that is, prepared as a cartridge.

This is because, when accommodated in such a coated member, not only the handling becomes easier but alto the loss caused by flow water can be prevented even when the antimicrobial glass is reduced to a small size according to use for a long period of time.

Further, with an antimicrobial glass as accommodated in advance in a coated member, a constant amount of an antimicrobial glass can be easily accommodated in the antimicrobial water unit 10 that is shown in FIGS. 2(*a*) and 2(*b*).

Meanwhile, the antimicrobial water unit 10 that is shown in FIGS. 2(*a*) and 2(*b*) is also a kind of a coated member.

Figure 12A:
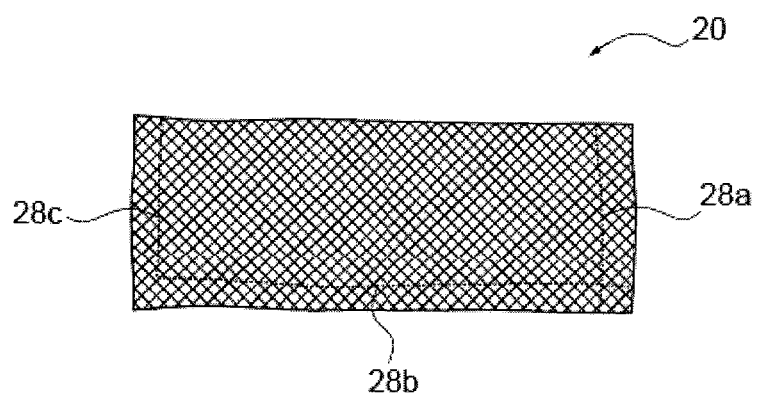
FIG. 12(a) and FIG. 12(b) are drawings which are provided for describing a coated member.
Figure 12B:
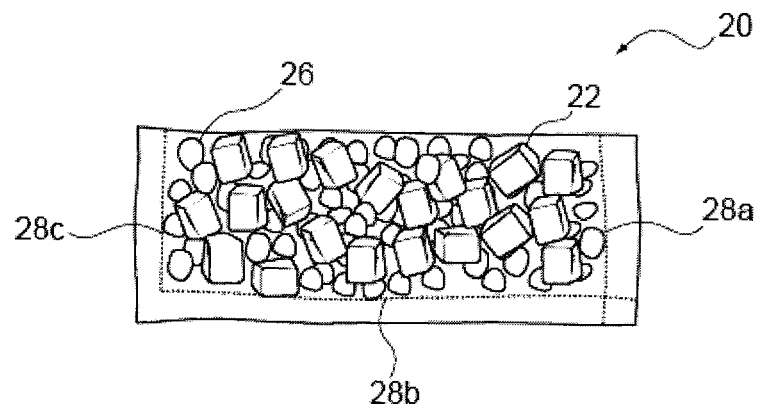

Furthermore, the coated member can be prepared as a mesh-like envelope product 20 as shown in FIGS. 12(*a*) and 12(*b*), for example.

More specifically, it preferably consists of a mesh having a hole size of 50 to 500 μm or so, which is composed of polypropylene or the like, and is prepared as an envelope product with a size of 105×45×17 mm or so.

Furthermore, the envelope product preferably has a mode in which the antimicrobial glass is accommodated while the seal part 28*b* and 28*c* are installed in advance and the seal part 28*a* is installed as a final step.

Meanwhile, the accommodation amount of the antimicrobial glass preferably has a value within the range of 10 to 30 g, and more preferably has a value within the range of 15 to 25 g.

Furthermore, as shown in FIG. 12(*b*), it is preferable that the antimicrobial glass 22 of the present invention is accommodated inside the coated member 20, together with the non-antimicrobial glass 26.

This is because, as it is accommodated together with a non-antimicrobial glass, binding between antimicrobial glasses is prevented so that a predetermined silver ion elution amount can be more stably maintained over a long period of time.

Meanwhile, the type of a non-antimicrobial glass is not particularly limited if it is a glass not allowing elution of silver ions upon dissolution in water. Preferred examples include, however, soda glass, borosilicate glass, lead glass (crystal glass), quartz glass, aluminum silicate glass, and phosphate glass.

More specifically, it is preferably a non-antimicrobial glass having, as a main component, soda glass obtained by adding $SiO_2$ or the like as a glass network component, within the range of 35 to 65% by weight and also, as a glass network-modifying component, at least one of $Na_2O$, $K_2O$, $Li_2O$, $CaO$, $MgO$, $BaO$, $B_2O_3$, and $Al_2O_3$ within the range of 15 to 45% by weight relative to the total amount.

Figure 13:
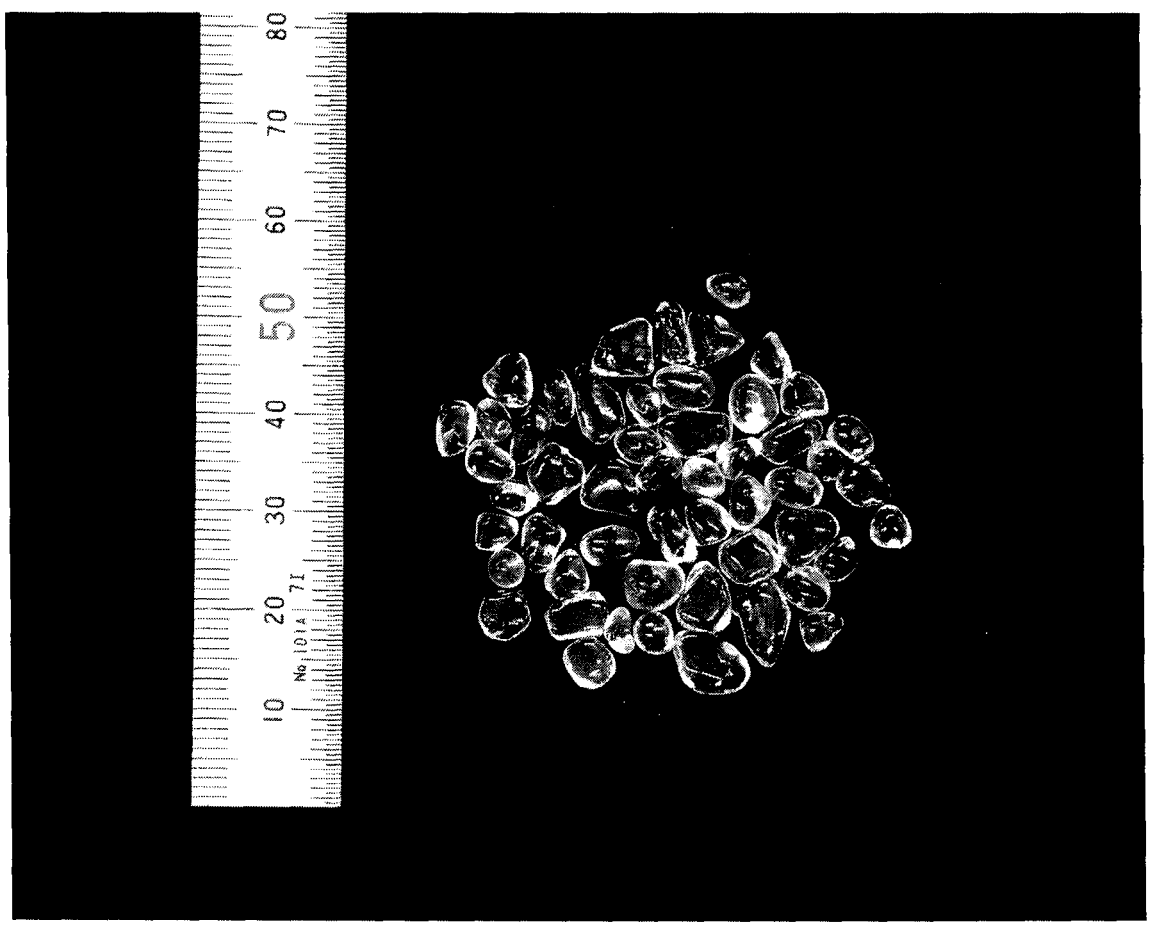
FIG. 13 is a drawing provided for describing the shape of a non-antimicrobial glass.

Furthermore, the shape of a non-antimicrobial glass is not particularly limited. However, it is preferably a non-antimicrobial glass with different shape as shown in FIG. 13, for example.

This is because, with such shape, not only easy molding can be achieved but also the balance weight effect for water flow can be effectively exhibited.

Furthermore, regarding the size of a non-antimicrobial glass, the maximum diameter preferably has a value within the range of 3 to 30 mm.

This is because such non-antimicrobial glass can have substantially the same maximum diameter as that of an antimicrobial glass so that it can be easily and homogeneously mixed with an antimicrobial glass while it is hardly get localized.

Furthermore, the blending amount of a non-antimicrobial glass preferably has a value within the range of 5 to 15% by weight relative to 100 parts by weight of an antimicrobial glass.

This is because, with such blending amount of a non-antimicrobial glass, not only a predetermined antimicrobial property of an antimicrobial glass can be exhibited but also the overall weight of a cartridge can be easily controlled.

Thus, from this point of view, the blending amount of a non-antimicrobial glass more preferably has a value within the range of 7 to 12 parts by weight, and even more preferably has a value within the range of 8 to 11 parts by weight relative to 100 parts by weight of an antimicrobial glass

EXAMPLES

Hereinbelow, the antimicrobial glass of the present invention is described in more detail by way of examples. However, the following examples are only to illustrate the present invention, and the present invention is not limited to those descriptions.

Example 1

1. Production of Antimicrobial Glass
(1) Melting Process

As an antimicrobial glass composition, a glass feedstock having the composition shown in Table 1 was stirred until uniformly mixed by using a universal mixer at a rotational speed of 250 rpm for 30 minutes.

Subsequently, using a glass melting furnace, the glass feedstock was heated at 1280° C. for 3.5 hours to produce molten glass.

(2) Molding Process

Figure 14A:
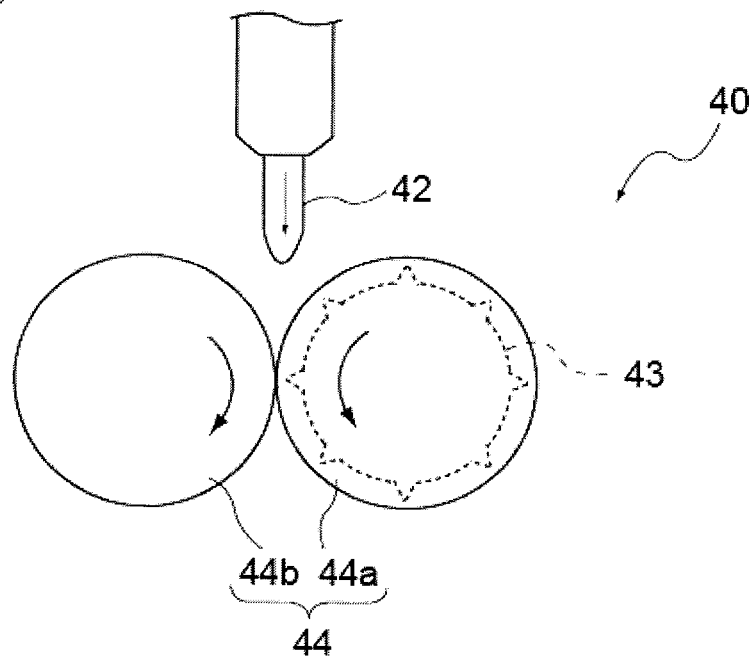
FIG. 14(a) and FIG. 14(b) are drawings which are provided for describing the process for producing an antimicrobial glass.
Figure 14B:
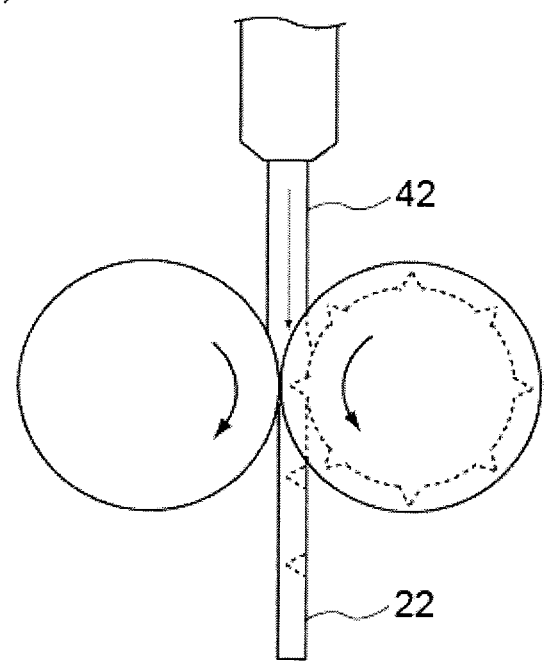

As shown in FIGS. 14(a) and 14(b), the molten glass 42 taken out from the glass melting furnace was introduced to the molding device 40, and thus the antimicrobial glass 22 in the form of tablet shape as shown in FIG. 11 (maximum diameter: 10 mm, surface area of one piece: 2.5 $cm^2$) was molded.

(3) Surface Grinding Process 500 g of the obtained antimicrobial glass in the form of tablet were charged into a vibration ball mill using no medium. Subsequently, 500 g of isopropyl alcohol was added, and the vibration ball mill was operated at room temperature for 30 minutes in that state, thereby carrying out the surface grinding process including deburring step.

As a result, although minute irregularities were found before the surface grinding process, the surface was smooth and glossy after the surface grinding process. The resulting glass was used as the final antimicrobial glass.

The specific surface area of the obtained antimicrobial glass was 3.75 $cm^2/g$.

2. Evaluation of Antimicrobial Glass
(1) Measurement of Reference Silver Ion Elution Amount The reference silver ion elution amount of the obtained antimicrobial glass was measured.

More specifically, 30 g of the obtained antimicrobial glass was immersed in 1 liter of purified water (30° C., pH 6.5), and allowed to stand in a closed system for 24 hours with the temperature maintained.

Subsequently, the silver ion elute was filtered through a filter paper (5C) to have a measurement sample, and then the silver ion concentration in the measurement sample was measured using a silver ion meter (manufactured by Toko Chemical Laboratories Co., Ltd., silver ion meter TiN-5104), and the reference silver ion elution amount in the antimicrobial glass (mg/(g·1 liter·24 Hrs·30° C.)) was calculated. The obtained results are listed in Table 2.

(2) Evaluation of Silver Ion Elution Amount after 7 Days

The silver ion elution amount in the obtained antimicrobial glass after 7 days was measured.

Namely, after measuring the reference silver ion elution amount described above, 1 liter of purified water containing eluted silver ions was discarded, the antimicrobial glass remained after dissolving was immersed in 1 liter of fresh purified water, and the antimicrobial glass was immersed in purified water at the same conditions as the conditions for measurement of the reference silver ion solution amount and allowed to stand for 5 days.

Subsequently, 1 liter of the purified water containing eluted silver ions was discarded, the antimicrobial glass remained after dissolving was immersed in 1 liter of fresh purified water, and after allowing it to stand for 24 hours at the same conditions as the conditions for measuring the reference silver ion elution amount, the result was used as the silver ion elution amount after 7 days (mg/(g·1 liter·24 Hrs·30° C.)). The obtained result is shown in Table 2.

(3) Evaluation of Silver Ion Elution Amount after 14 Days

The silver ion elution amount in the obtained antimicrobial glass after 14 days was measured.

Namely, after measuring the silver ion elution amount on Day 7 after immersion in purified water as described above, 1 liter of purified water containing eluted silver ions was discarded, the antimicrobial glass remained after dissolving was immersed in 1 liter of fresh purified water, and the antimicrobial glass was allowed to stand for 6 days at the same conditions as the conditions for measurement of the reference silver ion solution amount.

Subsequently, 1 liter of the purified water containing eluted silver ions was discarded, the antimicrobial glass remained after dissolving was immersed in 1 liter of fresh purified water, and after allowing it to stand for 24 hours at the same conditions as the conditions for measuring the reference silver ion elution amount, the silver ion elution amount was measured and the result was used as the silver ion elution amount after 14 days (mg/(g·1 liter·24 Hrs·30° C.)). The obtained result is shown in Table 2.

(4) Evaluation of Antimicrobial Property
(4)-1 Bacteria Halo Test

By using the obtained antimicrobial glass, the bacteria halo test (based on JIS L 1902) was performed.

Figure 15:
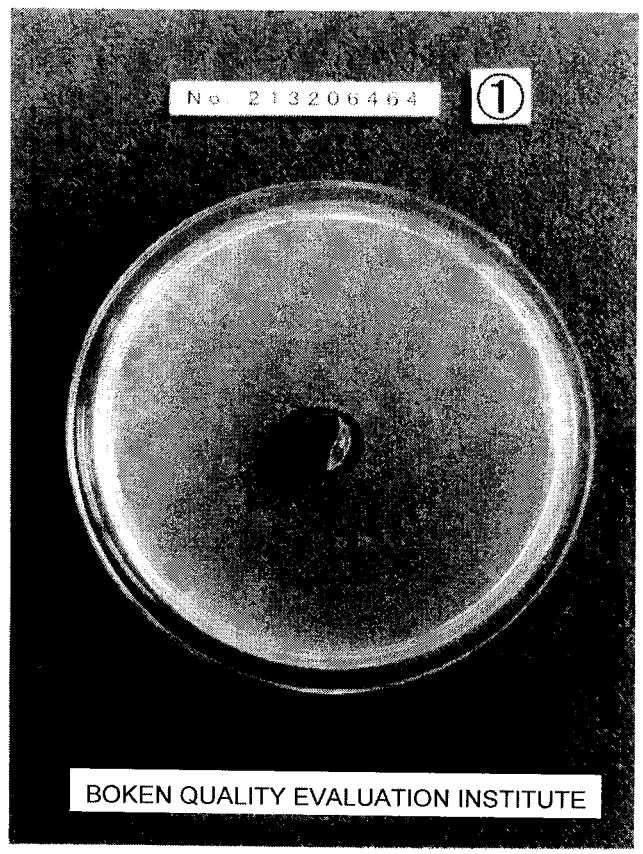
FIG. 15 is a photographic image provided for describing the halo test result of *Staphylococcus aureus*.

Namely, on a pour plate medium with *Staphylococcus aureus* (*Staphylococcus aureus* NBRC 12732), one of the obtained antimicrobial glasses was tightly adhered followed by culture for 24 hours in an environment of 37±2° C. Thereafter, width (mm) of a transparent zone of growth inhibition (halo) occurred near the antimicrobial glass was measured. The obtained result is shown in Table 1. Furthermore, the photographic image of the pour plate medium obtained therefrom was shown in FIG. 15.

Figure 16:
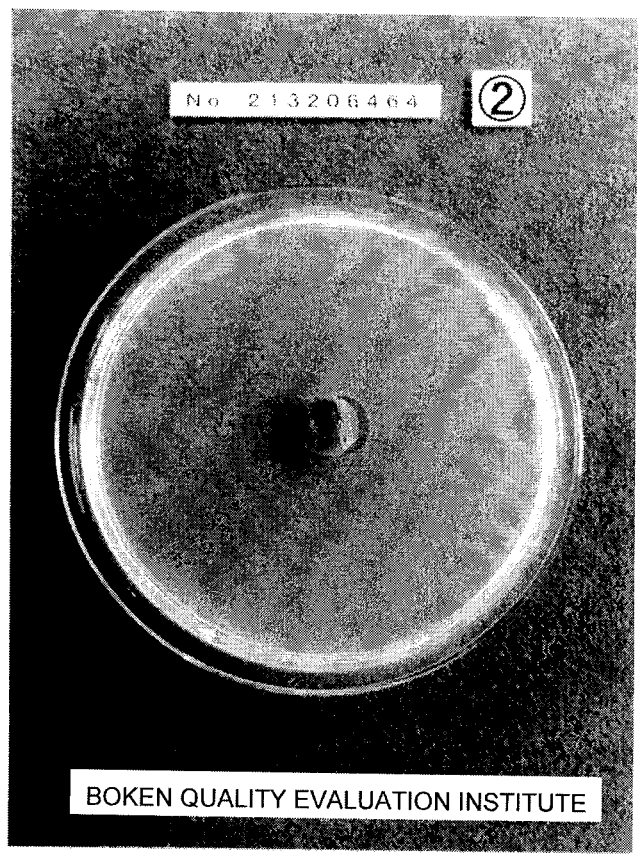
FIG. 16 is a photographic image provided for describing the halo test result of *Escherichia coli*.

In addition, the halo test was also carried out by using *Escherichia coli* (*Escherichia coli* NBRC 3301) instead of *Staphylococcus aureus*. The obtained result is shown in Table 2. Furthermore, the photographic image of the pour plate medium obtained therefrom was shown in FIG. 16.

(4)-2 Mold Halo Test

By using the obtained antimicrobial glass, the mold halo test (based on JIS L 1902) was performed.

Figure 17:
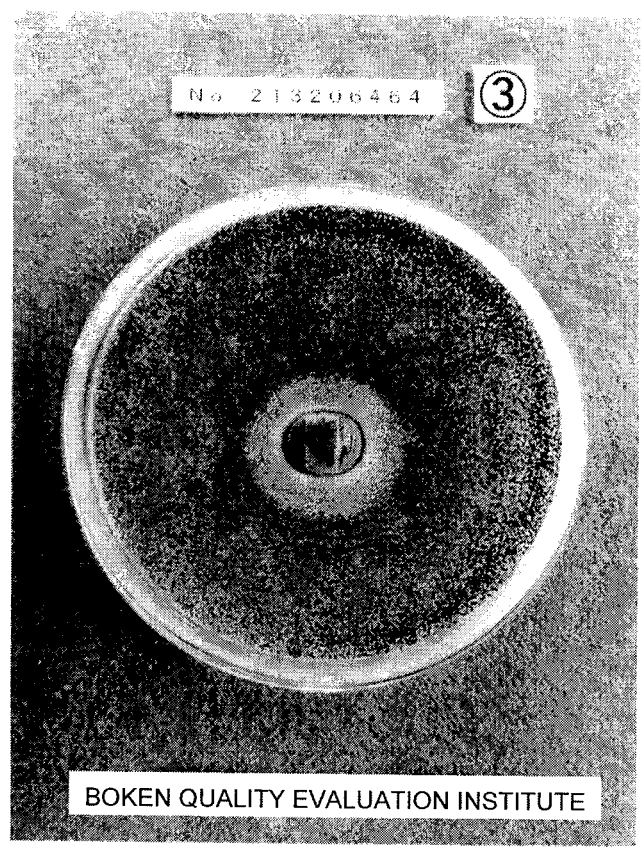
FIG. 17 is a photographic image provided for describing the halo test result of *Aspergillus niger*.

Namely, on a plate medium which has been inoculated with *Aspergillus niger* (*Aspergillus niger* NBRC 105649), one of the obtained antimicrobial glasses was tightly adhered followed by culture for 24 hours in an environment of 28±2° C. Thereafter, width (mm) of a transparent zone of growth inhibition (halo) occurred near the antimicrobial glass was measured. The obtained result is shown in Table 2. Furthermore, the photographic image of the plate medium obtained therefrom was shown in FIG. 17.

Figure 18:
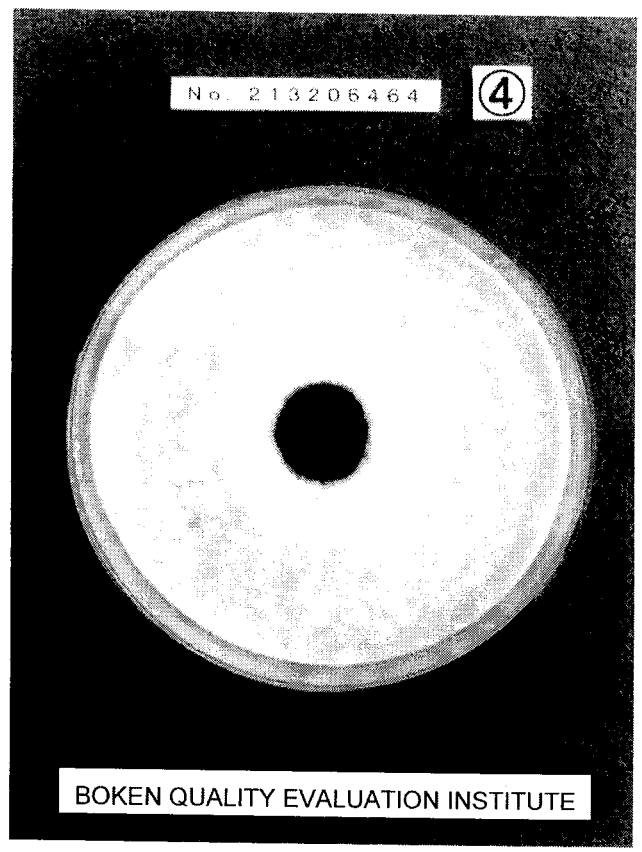
FIG. 18 is a photographic image provided for describing the halo test result of *Penicillium*.
Figure 19:
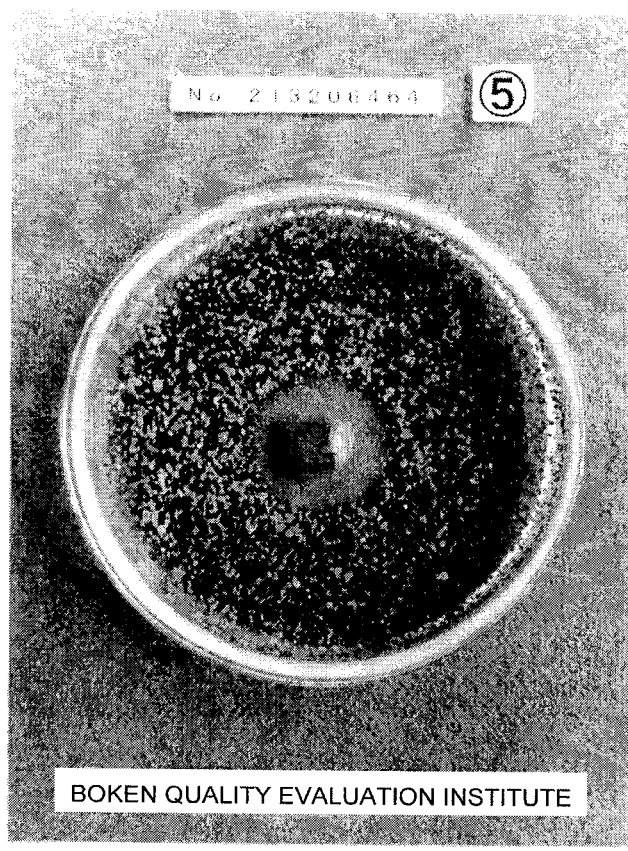
FIG. 19 is a photographic image provided for describing the halo test result of black mold.
Figure 20:
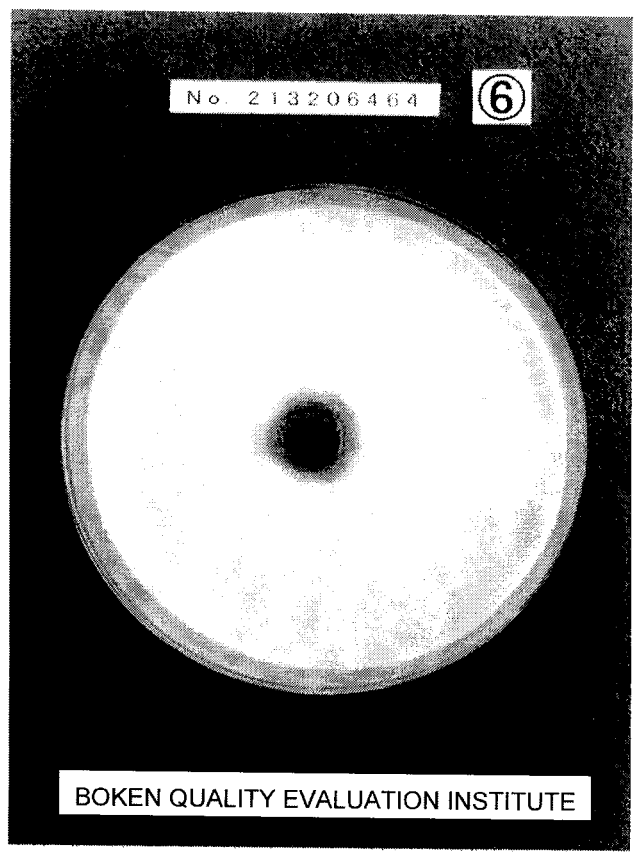
FIG. 20 is a photographic image provided for describing the halo test result of *Trichophyton*.

In addition, the halo test was also carried out by using each of *Penicillium* (*Penicillium citrinum* NBRC 6352), black mold (*Cladosporium cladosporioides* NBRC 6348) and *Trichophyton* (*Trichophyton mentagrophytes* NBRC 32409) instead of *Aspergillus niger*. The obtained result is shown in Table 2. Furthermore, the photographic image of the plate medium obtained therefrom was shown in each of FIGS. 18, 19 and 20.

Meanwhile, the aforementioned evaluation of antimicrobial property was performed only in Example 1.

(5) Evaluation of Occurrence of Black Mold or the Like in Washing Tub

The obtained antimicrobial glass was actually applied to a washing machine, and an occurrence of black mold or the like in washing tub was evaluated.

Namely, 20 g of the obtained antimicrobial glass was accommodated in an antimicrobial water unit of a drum type washing machine as shown in FIG. 1(*a*), and 5 kg of a subject for washing (white underwear made of cotton) was washed once a day for 100 days from June to September.

Subsequently, after washing for 100 days, an occurrence of black mold or the like on a backside of the washing tub was observed with a naked eye, and evaluated according to the following criteria. The obtained result is shown in Table 2.

⊙: Black mold or the like is not observed at all.
○: Black mold or the like is hardly observed.
Δ: Black mold or the like is somewhat observed.
x: Black mold or the like is clearly observed.

(6) Evaluation of Antimicrobial Property and Coloration Property of Subject for Washing The obtained antimicrobial glass was actually applied to a washing machine, and the antimicrobial property and coloration property of a subject for washing were evaluated.

Namely, the white cotton underwear after washing for 100 days, which has been obtained after performing the evaluation of an occurrence of black mold or the like in washing tub as described above, was allowed to stand for 48 hours under exposure to sunlight in an environment including temperature of 35° C. and humidity of 95% Rh. Then, it was subjected to an evaluation of antimicrobial property and coloration property according to the following criteria. The obtained result is shown in Table 2.

⊙: Malodor and darkish color are not observed at all.
○: Malodor or darkish color is hardly observed.
Δ: Malodor or darkish color is somewhat observed.
x: Malodor or darkish color is clearly observed.

Example 2

According to Example 2, an antimicrobial glass was produced and evaluated in the same manner as Example 1 except that, with regard to a composition of an antimicrobial glass, the contents of $Ag_2O$ and CoO were maintained but the content of ZnO was reduced to 4.05% by weight and ratio of other components was increased as much as the reduced content of ZnO, as shown in Table 1. The obtained result is shown in Table 1.

Example 3

According to Example 3, an antimicrobial glass was produced and evaluated in the same manner as Example 1 except that, with regard to a composition of an antimicrobial glass, the contents of $Ag_2O$ and CoO were maintained but the content of ZnO was reduced to 0% by weight and ratio of other components was increased as much as the reduced content of ZnO, as shown in Table 1. The obtained result is shown in Table 1.

Comparative Example 1

According to Comparative Example 1, an antimicrobial glass was produced and evaluated in the same manner as Example 1 except that, with regard to a composition of an antimicrobial glass, the contents of $Ag_2O$ and CoO were maintained but the content of ZnO was increased to 14.05% by weight and ratio of other components was decreased as much as the increased content of ZnO, as shown in Table 1. The obtained result is shown in Table 1.

Comparative Example 2

According to Comparative Example 2, an antimicrobial glass was produced and evaluated in the same manner as Example 1 except that, with regard to a composition of an antimicrobial glass, the contents of $Ag_2O$ and CoO were maintained but the content of ZnO was increased to 19.05% by weight and ratio of other components was decreased as much as the increased content of ZnO, as shown in Table 1. The obtained result is shown in Table 1.

Comparative Example 3

According to Comparative Example 3, an antimicrobial glass was produced and evaluated in the same manner as Example 1 except that the composition of an antimicrobial glass was modified to have the composition shown in Table 1. The obtained result is shown in Table 1.

Meanwhile, the antimicrobial glass of Comparative Example 3 is a type of an antimicrobial glass with large silver ion elution amount, which is used for a drain pan of an air conditioner.

Comparative Example 4

According to Comparative Example 4, an antimicrobial glass was produced and evaluated in the same manner as Example 1 except that the composition of an antimicrobial glass was modified to have the composition shown in Table 1. The obtained result is shown in Table 1.

Meanwhile, the antimicrobial glass of Comparative Example 4 is a type of an antimicrobial glass with small silver ion elution amount, which has been conventionally used for an antimicrobial water unit of a washing machine.

TABLE 1

| | Composition of antimicrobial glass | | | | | | | | | | | |
|---|---|---|---|---|---|---|---|---|---|---|---|---|
| | $Ag_2O$ (% by weight) | $P_2O_5$ (% by weight) | CaO (% by weight) | ZnO (% by weight) | $K_2O$ (% by weight) | $Al_2O_3$ (% by weight) | MgO (% by weight) | $Na_2O$ (% by weight) | $B_2O_3$ (% by weight) | $CeO_2$ (% by weight) | CoO (% by weight) | C2/C1 (—) |
| Example 1 | 6.00 | 62.65 | 2.30 | 9.05 | 8.00 | 3.92 | 8.00 | 0.00 | 0.00 | 0.00 | 0.08 | 0.433 |
| Example 2 | 6.00 | 63.65 | 3.30 | 4.05 | 9.00 | 4.92 | 9.00 | 0.00 | 0.00 | 0.00 | 0.08 | 1.215 |
| Example 3 | 6.00 | 64.46 | 4.11 | 0.00 | 9.81 | 5.73 | 9.81 | 0.00 | 0.00 | 0.00 | 0.08 | — |
| Comparative Example 1 | 6.00 | 61.65 | 1.30 | 14.05 | 7.00 | 2.92 | 7.00 | 0.00 | 0.00 | 0.00 | 0.08 | 0.208 |

TABLE 1-continued

| | Composition of antimicrobial glass | | | | | | | | | | |
|---|---|---|---|---|---|---|---|---|---|---|---|
| | $Ag_2O$ (% by weight) | $P_2O_5$ (% by weight) | CaO (% by weight) | ZnO (% by weight) | $K_2O$ (% by weight) | $Al_2O_3$ (% by weight) | MgO (% by weight) | $Na_2O$ (% by weight) | $B_2O_3$ (% by weight) | $CeO_2$ (% by weight) | CoO (% by weight) | C2/C1 (—) |
| Comparative Example 2 | 6.00 | 60.65 | 0.30 | 19.05 | 6.00 | 1.92 | 6.00 | 0.00 | 0.00 | 0.00 | 0.08 | 0.101 |
| Comparative Example 3 | 6.00 | 57.80 | 0.00 | 13.80 | 14.00 | 0.00 | 6.70 | 1.70 | 0.00 | 0.00 | 0.03 | 0 |
| Comparative Example 4 | 3.04 | 66.80 | 21.99 | 0.00 | 0.00 | 2.00 | 0.00 | 0.60 | 5.00 | 0.52 | 0.05 | — |

TABLE 2

| | Reference silver ion elution amount (mg/ (g · 1 liter · 24 Hrs · 30° C.)) | Silver ion elution amount after 7 days (mg/(g ·1 liter · 24 Hrs · 30° C.)) | Silver ion elution amount after 14 days (mg/(g ·1 liter · 24 Hrs · 30° C.)) | Antimicrobial property (halo width) (mm) | | | | | | Occurrence of black mold in washing tub | Antimicrobial property and coloration property of subject for washing |
|---|---|---|---|---|---|---|---|---|---|---|---|
| | | | | Staphylococcus aureus | Escherichia coli | Aspergillus niger | Penicillium | Black mold | Trichophyton | | |
| Example 1 | 0.063 | 0.039 | 0.030 | 3.3 | 3.0 | 2.0 | 3.5 | 4.8 | 0.5 | ○ | ○ |
| Example 2 | 0.055 | 0.046 | 0.033 | | | | | | | Δ | ○ |
| Example 3 | 0.048 | 0.036 | 0.029 | | | | | | | Δ | ○ |
| Comparative Example 1 | 0.125 | 0.116 | 0.115 | | | | | | | ◎ | x |
| Comparative Example 2 | 0.255 | 0.219 | 0.234 | | | | | | | ◎ | x |
| Comparative Example 3 | 0.303 | 0.251 | 0.255 | | | | | | | ◎ | x |
| Comparative Example 4 | 0.023 | 0.019 | 0.024 | | | | | | | ○ | ○ |

INDUSTRIAL APPLICABILITY

According to the antimicrobial glass of the present invention, as the composition of an antimicrobial glass for releasing silver ion when brought into direct contact with water is set to a predetermined composition and the shape and maximum diameter of the glass are adjusted to be in a predetermined range, it is possible to stably maintain a predetermined elution amount of silver ions over a long period of time, even if it is a compact amount.

As a result, it can be stored in a narrow accommodation space in an antimicrobial water unit for supplying antimicrobial water to a washing tub of a washing machine, an occurrence of black mold or the like in a washing tub can be effectively suppressed, and a subject for washing can be effectively protected against microbes while suppressing the coloration of the subject.

As such, the antimicrobial glass of the present invention is expected to significantly contribute to achieving high quality of an antimicrobial glass for a washing machine, in particular.

EXPLANATIONS OF LETTERS OR NUMERALS

1a: Drum type washing machine
1b: Stand type washing machine
2: Washing tub
3: Cover
4: Circulating water path
6: Part of wall surface of washing tub
10: Antimicrobial water unit
12: Opening
14: Fixing hole
16: Hinge part
18: Lock part
20: Coated member
22: Antimicrobial glass
26: Non-antimicrobial glass
28: Seal part,
40: Molding device
42: Molten glass

What is claimed is:

1. An antimicrobial water unit consisting of
   (i) a housing member adapted to house glass tablets; and
   (ii) glass tablets housed within said housing member, said glass tablets consisting of antimicrobial glass;
where the glass tablets have a maximum diameter of 5 to 20 mm,
where the antimicrobial glass that releases silver ions when brought into direct contact with water, and where the antimicrobial glass consists of, based upon the total weight of the antimicrobial glass;
   $Ag_2O$ in the range 5.5 to 10 wt %;
   $P_2O_5$ in the range 55 to 75 wt %;
   $CaO$ in the range 2 to 10 wt %;
   $K_2O$ in the range 5 to 20 wt %;
   $Al_2O_3$ in the range 1 to 10 wt %;
   $MgO$ in the range 5 to 20 wt %; and
   $ZnO$ in the range 4 to 9.5 wt %,
and where said antimicrobial glass has a silver ion elution amount in the range of 0.025 to 0.08 mg/g·liter, over 24 hours at 30° C., which is measured by immersing 30 g of the antimicrobial glass in 1 liter of purified water at a temperature of 30° C. and a pH of 6.5, maintaining the glass within a closed system for 24 hours with the temperature maintained, and then taking the measurement.

2. The antimicrobial water unit of claim 1, where the antimicrobial water unit is adapted to be positioned within a circulating water path of a washing machine.

3. The antimicrobial water unit of claim 1, where the housing member is a mesh envelope.

4. The antimicrobial water unit of claim 1, where the housing member is a plastic coated member.

5. An antimicrobial water unit consisting of
   (i) a housing member adapted to house glass tablets; and
   (ii) glass tablets housed within said housing member, said glass tablets consisting of antimicrobial glass and non-antimicrobial glass;
where the glass tablets have a maximum diameter of 5 to 20 mm,
where the antimicrobial glass releases silver ions when brought into direct contact with water,
and where the antimicrobial glass consists of, based upon the total weight of the antimicrobial glass,
   $Ag_2O$ in the range 5.5 to 10 wt %;
   $P_2O_5$ in the range 55 to 75 wt %;
   $CaO$ in the range 2 to 10 wt %;
   $K_2O$ in the range 5 to 20 wt %;
   $Al_2O_3$ in the range 1 to 10 wt %;
   $MgO$ in the range 5 to 20 wt %; and
   $ZnO$ in the range 4 to 9.5 wt %,
and where said antimicrobial glass has a silver ion elution amount in the range of 0.025 to 0.08 mg/g·liter, over 24 hours at 30° C., which is measured by immersing 30 g of the antimicrobial glass in 1 liter of purified water at a temperature of 30° C. and a pH of 6.5, maintaining the glass within a closed system for 24 hours with the temperature maintained, and then taking the measurement.

6. The antimicrobial water unit of claim 5, where the antimicrobial water unit is adapted to be positioned within a circulating water path of a washing machine.

7. The antimicrobial water unit of claim 5, where the housing member is a mesh envelope.

8. The antimicrobial water unit of claim 5, where the housing member is a plastic coated member.

* * * * *